US010344085B2

(12) United States Patent
Dengl et al.

(10) Patent No.: US 10,344,085 B2
(45) Date of Patent: Jul. 9, 2019

(54) ANTI-IL-1BETA ANTIBODIES

(71) Applicant: Hoffmann-La Roche Inc., Little Falls, NJ (US)

(72) Inventors: Stefan Dengl, Munich (DE); Peter Michael Huelsmann, Habach (DE); Christian Gassner, Penzberg (DE); Sebastian Breuer, Penzberg (DE); Olaf Mundigl, Weilheim (DE); Guy Georges, Habach (DE); Ralf Schumacher, Penzberg (DE); Guido Hartmann, Loerrach (DE); Sabine Gruener, Grenzach-Wyhlen (DE)

(73) Assignee: Hoffman-La Roche, Inc., Little Falls, NJ (US)

( * ) Notice: Subject to any disclaimer, the term of this patent is extended or adjusted under 35 U.S.C. 154(b) by 0 days.

(21) Appl. No.: 15/590,161

(22) Filed: May 9, 2017

(65) Prior Publication Data
US 2017/0247447 A1    Aug. 31, 2017

Related U.S. Application Data

(63) Continuation of application No. PCT/EP2015/075875, filed on Nov. 6, 2015.

(30) Foreign Application Priority Data

Nov. 10, 2014 (EP) ..................... 14192523

(51) Int. Cl.
C07K 16/24   (2006.01)
C07K 16/22   (2006.01)
A61K 39/00   (2006.01)

(52) U.S. Cl.
CPC .......... C07K 16/245 (2013.01); C07K 16/22 (2013.01); A61K 2039/507 (2013.01); C07K 2299/00 (2013.01); C07K 2317/24 (2013.01); C07K 2317/31 (2013.01); C07K 2317/33 (2013.01); C07K 2317/55 (2013.01); C07K 2317/56 (2013.01); C07K 2317/73 (2013.01); C07K 2317/76 (2013.01); C07K 2317/92 (2013.01); C07K 2317/94 (2013.01)

(58) Field of Classification Search
CPC .................................... C07K 16/245
See application file for complete search history.

(56) References Cited

U.S. PATENT DOCUMENTS

| 4,935,343 | A  | 6/1990  | Allison et al. |
| 8,268,314 | B2 | 9/2012  | Baehner et al. |
| 8,703,130 | B2 | 4/2014  | Baehner et al. |
| 9,151,761 | B2 | 10/2015 | Anderson et al. |
| 9,695,233 | B2 | 7/2017  | Duerr et al. |
| 9,708,396 | B2 | 7/2017  | Baehner et al. |
| 2010/0111967 | A1 | 5/2010 | Baehner et al. |
| 2012/0321627 | A1 | 12/2012 | Baehner et al. |
| 2014/0093498 | A1 | 4/2014  | Gschwind et al. |
| 2014/0093499 | A1 | 4/2014  | Gschwind et al. |
| 2014/0348824 | A1 | 11/2014 | Anderson et al. |
| 2015/0004166 | A1 | 1/2015  | Baehner et al. |
| 2015/0232548 | A1 | 8/2015  | Klein et al. |
| 2017/0240629 | A1 | 8/2017  | Bedoucha et al. |
| 2017/0247440 | A1 | 8/2017  | Bedoucha et al. |
| 2017/0247441 | A1 | 8/2017  | Dengl et al. |
| 2017/0247447 | A1 | 8/2017  | Dengl et al. |
| 2017/0369566 | A1 | 12/2017 | Baehner et al. |
| 2018/0134780 | A1 | 5/2018  | Klein et al. |
| 2018/0346559 | A1 | 12/2018 | Hilberg et al. |
| 2019/0004048 | A1 | 1/2019  | Anderson et al. |

FOREIGN PATENT DOCUMENTS

| WO | 2004/003019 A2 | 8/2004 |
| WO | 2004/067568 A2 | 8/2004 |
| WO | 2005/087812 A1 | 9/2005 |
| WO | 2008/024188 A2 | 2/2008 |
| WO | 2010/040508 A1 | 4/2010 |
| WO | 2011/117329 A1 | 9/2011 |
| WO | 2014/001442 A1 | 1/2014 |
| WO | 2014/009465    | 1/2014 |
| WO | 2014/072876 A1 | 5/2014 |
| WO | 2014/074823 A1 | 5/2014 |
| WO | 2014/109999 A1 | 7/2014 |
| WO | 2014/177460    | 11/2014 |
| WO | 2015/107026 A1 | 7/2015 |

OTHER PUBLICATIONS

Hessen et al., "Dry Eye: and Inflammatory Ocular Disease" Journal of Ophthalmic and Vision Research 9(2):240-250 ( 2014).
IPRP for PCT/EP2015/075879 (dated May 16, 2017).
ISR for PCT/EP2015/075879 (dated Dec. 21, 2015).
Jo, N. et al., "Inhibition of Platelet-Derived Growth Factor B Signaling Enhances the Efficacy of Anti-Vascular Endothelial Growth Factor Therapy in Multiple Models of Ocular Neovascularization" American Journal of Pathology 168(6):2036-2053 ( 2006).
Kienast et al., "Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy" Clin Cancer Res 19(24):6730-6740 (Dec. 15, 2013).
Kontermann, "Dual targeting strategies with bispecific antibodies" mAbs (Mar./Apr. 2012), 4(2):182-197.
Leonardzehr et al., "Molecular Partners continues to validate DARPin platform" BioTuesdays:1-8 ( 2012).
Li, Q. et al., "Therapeutic efficacy of three bispecific antibodies on collagen-induced arthritis mouse model" International Immunopharmacology 21:119-127 ( 2014).

(Continued)

Primary Examiner — Prema M Mertz
(74) Attorney, Agent, or Firm — Grant Kalinowski

(57) ABSTRACT

Herein are reported humanized anti-IL-1beta antibodies that are humanized variants of the murine anti-IL-1beta antibody H34. A specific humanized antibody comprises (a) a HVR-H1 comprising the amino acid sequence of SEQ ID NO: 25, (b) a HVR-H2 comprising the amino acid sequence of SEQ ID NO: 27, and (c) a HVR-H3 comprising the amino acid sequence of SEQ ID NO: 28.

9 Claims, No Drawings

Specification includes a Sequence Listing.

(56) References Cited

OTHER PUBLICATIONS

Mabry, R. et al., "A dual-targeting PDGFRβ/VEGF-A molecule assembled from stable antibody fragments demonstrates anti-angiogenic activity in vitro and in vivo" mAbs 2(1):20-34 (2010).
Papadopoulos, K.P. et al., "A phase I first-in-human study of REGN910 (SAR307746), a fully human and selective angiopoietin-2 (Ang2) monoclonal antibody (MAb), in patients with advanced solid tumor malignancies" Abstract (Abstract 2517) ASCO Annual Meeting, (2013) http://meetinglibrary.asco.org/print/1155681
Planck et al., "Impact of IL-1 signalling on experimental uveitis and arthritis" Ann Rheum Dis 71(5):753-760 (2012).
Schaefer et al., "Immunoglobulin domain crossover as a generic approach for the production of bispecific IgG antibodies" Proceedings of the National Academy of Sciences 108(27):11187-11192 (Jul. 5, 2011).
Solomon et al., "Pro- and Anti-inflammatory Forms of Interleukin-1 in the Tear Fluid and Conjuctiva of Patients with Dry Eye Disease" Investigative Ophthalmology & Visual Science 42(10):2283-2292 (2001)
Thomas et al., "A Novel Angiopoietin-2 Selective Fully human Antibody with Potent Anti-Tumoral and Anti-Angiogenic Efficacy and Superior Side Effect Profile Compared to Pan-Angiopoietin-1/2 Inhibitors" PLOS-One 8(2):e54923 (Feb. 2013).
Vassbotn, F.S. et al., "A monoclonal antibody against PDGF B-chain inhibits PDGF-induced DNA synthesis in C3H fibroblasts and prevents binding of PDGF to its receptor" Biochimica et Biophysica Acta 1054(2):246-249 (1990).
Wu, C. et al., "Molecular construction and optimization of anti-human IL-1α/β dual variable domain immunoglobulin (DVD-IgTM) molecules" mAbs 1(4):339-347 (2009).
Bessho et al., "Effect of Ang-2-VEGF-A bispecific antibody in renal cell carcinoma" Cancer Investigation 33(8):378-86 (2015).
Bezuidenhout et al., "Association of Ang-2 with Integrin β2 Controls Ang-2/PDGF-BB-Dependent Upregulation of Human Peripheral Blood Monocyte Fibrinolysis" Inflammation 32(6):393 (2009).
Bezuidenthout et al., "Ang-2 and PDGD-BB cooperatively stimulate human peropheral Blood monocyte fibrinolysis" Journal of Leukoeyte Biology 81:1496 (2007).
Bogdanovic et al., "Activation of Tie2 by angiopoietin-1 and angiopoietin-2 results in their release and receptor internalization" J. Cell Sci. 119(17):3551-33560 (2006).
Fenn, S. st al., "Crystal Structure of an Anti-Ang2 CrossFab Demonstrates Complete Structural and Functional Integrity of the Variable Domain" PLOS ONE 8(4):e61953 (Apr. 1, 2013).
Gassner, C. et al., "Development and validation of a novel SPR-based assay principle for bispecific molecules" Journal of Pharmaceutical and Biomedical Analysis 102:144-149 (2015).
Hasen et al., "Effects of angiopoietins-1 and -2 in the receptor tyrosine kinase Tie2 are differentially regulated at the endothelial cell surface" Cell Signal 22(3):527-532 (2010).
Klein et al., "The use of the CrossMAb technology for the generation of bi-and multispecific antibodies" MABS 8(6):1010-1020 (2016).
Kloepper et al., "Ang-2/VEGF bispecific antibody reprograms macrophages and resident microglia to anti-tumor phenotype and prolongs glioblastoma survival" Proc. Natl. Acad. Sci. USA 113(16):4476-4481 (2016).
Regula et al., "Targeting key angiogenic pathways with a bispecific CrossMAB optimized for neovascular eye disease" EMBO Molecular Medicine 8(11):1265 (2016).
Scheuer et al., "Anti-tumoral, anti-angiogenic and anti-metastatic efficacy of a tetravalent bispecific antibody (TAvi6) targeting VEGF-A and angiopoietin-2" MABS 8(3):562-573 (2016).
Stubenrauch et al., "An immunodepletion procedure advnces free angiopoietin-2 determination in human plasma samples during anti-cancer therapy with bispecific anti-Ang2/VEGF Cross Mab" J. of Pharm and Biomedical Analysis 102:459-67 (2015).
Ward et al., "Binding activities of a repertoire of single immunoglobulin variable domains"NATURE 341:544-546 (Oct. 12, 1989).

ANTI-IL-1BETA ANTIBODIES

CROSS REFERENCE TO RELATED APPLICATIONS

This application is a continuation of International Patent Application No. PCT/EP2015/075875 having an international filing date of Nov. 6, 2015, the entire contexts of which are incorporated herein by reference, and which claims benefit under 35 U.S.C. 119 to European Patent Application No. 14192523.0 filed Nov. 10, 2014.

SEQUENCE LISTING

The instant application contains a Sequence Listing which has been submitted electronically in ASCII format and is hereby incorporated by reference in its entirety. Said ASCII copy, created on May 1, 2017 is named P32414_US_Sequence_Listing.txt and is 48,448 bytes in size.

FIELD OF THE INVENTION

The present invention relates to anti-IL-1beta antibodies and methods of using the same.

BACKGROUND

Lymphokines like IL-1 are of multicellular origin, and through their multifaceted regulatory actions they affect a variety of different target cells during host response to infections. IL-1 at the site of inflammation activates lymphocytes, granulocytes, and fibroblasts. Moreover, IL-1 also may act as mediator of the acute-phase response, promote catabolism of structural protein and matrix and regulate the febrile response.

Two proteins that share human Interleukin-1 (IL-1) activity but are structurally distinct molecules have been identified. These proteins, termed IL-1alpha and IL-1beta, compete with one another for binding to IL-1 receptors and mediate similar biological activities. Both molecules are synthesized as large precursors (MW about 30,000 Da) that are processed to smaller biologically active forms (MW about 17,500 Da). However, they are encoded by two distinct complementary DNAs, show only a 26% amino acid homology, and have pI's (isoelectric pH's) of 5 and 7, respectively.

In U.S. Pat. No. 4,935,343 monoclonal antibodies which bind to IL-theta and do not bind to IL-1alpha (see also Kenney et J. Immunol. 138 (1987) 4236-4242). The antibodies bind to IL-1beta and block receptor binding to, and biological activity of, IL-1beta.

WO 2004/067568 reports human IL-1beta antagonists.

SUMMARY

The invention provides anti-IL-1beta antibodies and methods of using the same. In specific embodiments the antibody is a humanized antibody. In some of the humanized antibodies degradation hotspots have been removed to ensure improvements in developability of the antibody for large-scale production.

One aspect as reported herein is an isolated antibody that binds to human and cynomolgus IL-1beta, wherein the antibody is a humanized variant of a murine antibody whereby the murine antibody comprises a heavy chain variable domain of SEQ ID NO: 01 and a light chain variable domain of SEQ ID NO: 02.

One aspect as reported herein is a humanized antibody that specifically binds to human and cynomolgus IL-1beta, wherein the humanized antibody comprises (a) a HVR-H1 comprising the amino acid sequence of SEQ ID NO: 18, (b) a HVR-H2 comprising the amino acid sequence of SEQ ID NO: 20, and (c) a HVR-H3 comprising the amino acid sequence of SEQ ID NO: 21.

One aspect as reported herein is a humanized antibody that specifically binds to human and cynomolgus IL-1beta, wherein the humanized antibody comprises (a) a HVR-H1 comprising the amino acid sequence of SEQ ID NO: 25, (b) a HVR-H2 comprising the amino acid sequence of SEQ ID NO: 27, and (c) a HVR-H3 comprising the amino acid sequence of SEQ ID NO: 28.

One aspect as reported herein is a humanized antibody that specifically binds to human and cynomolgus IL-1beta, wherein the humanized antibody comprises (a) a HVR-H1 comprising the amino acid sequence of SEQ ID NO: 32, (b) a HVR-H2 comprising the amino acid sequence of SEQ ID NO: 34, and (c) a HVR-H3 comprising the amino acid sequence of SEQ ID NO: 35.

In one embodiment of all aspects as reported herein the humanized antibody further comprises (a) a HVR-L1 comprising the amino acid sequence of SEQ ID NO: 15; (b) a HVR-L2 comprising the amino acid sequence of SEQ ID NO: 16; and (c) HVR-L3 comprising the amino acid sequence of SEQ ID NO: 17.

In one embodiment of all aspects as reported herein the humanized antibody further comprises in the heavy chain variable domain at position 48 an isoleucine amino acid residue, at position 67 an alanine amino acid residue, at position 69 a phenylalanine amino acid residue and at position 93 a valine amino acid residue and comprising in the light chain variable domain at position 36 the amino acid residue serine (numbering according to Kabat).

In one embodiment of all aspects as reported herein the humanized antibody comprises (a) a VH sequence having at least 95% sequence identity to the amino acid sequence of SEQ ID NO: 04, (b) a VL sequence having at least 95% sequence identity to the amino acid sequence of SEQ ID NO: 06, or (c) a VH sequence as in (a) and a VL sequence as in (b).

In one preferred embodiment the humanized antibody comprises a VH sequence of SEQ ID NO: 04 and a VL sequence of SEQ ID NO: 06.

In one embodiment of all aspects as reported herein the humanized antibody is of the human subclass IgG1 or the human subclass IgG4.

In one embodiment of all aspects as reported herein the humanized antibody is of the human subclass IgG1 with a kappa light chain.

In one embodiment of all aspects as reported herein the humanized antibody is a monoclonal antibody.

One aspect as reported herein is an antibody comprising a VH sequence of SEQ ID NO: 04 and a VL sequence of SEQ ID NO: 06.

In one embodiment the antibody is a bispecific antibody.

In one embodiment of all aspects the humanized antibody specifically binds to human IL-1beta but does not bind to human IL-1alpha.

In one embodiment of all aspects the humanized antibody blocks the biological activity of human IL-1beta by inhibiting the binding of human IL-1beta to human IL-1 receptors.

In one embodiment of all aspects as reported herein the humanized antibody as reported herein specifically binds to two determinant sites on or close to the receptor binding site of IL-1beta.

In one preferred embodiment of all aspects the humanized antibody as reported herein blocks the interaction of IL-1R1 and IL-1RAcP with IL-1beta.

In one preferred embodiment of all aspects as reported herein the humanized antibody as reported herein blocks the formation of the IL-1 beta signaling complex at the first step of its assembly (i.e. it blocks the association of IL-1 beta and the IL-1R1).

One aspect as reported herein is an (isolated) nucleic acid encoding the antibody as reported herein.

One aspect as reported herein is a host cell comprising the nucleic acid as reported herein.

One aspect as reported herein is a method of producing an antibody as reported herein comprising culturing the host cell as reported herein to produce the antibody and recovering the antibody from the host cell or the cultivation medium.

One aspect as reported herein is a pharmaceutical formulation comprising an antibody as reported herein and a pharmaceutically acceptable carrier.

In one embodiment the pharmaceutical formulation further comprises an additional therapeutic agent. In one embodiment the additional therapeutic agent is an anti-ANG2 antibody or an anti-VEGF antibody.

One aspect as reported herein is the antibody as reported herein for use as a medicament.

One aspect as reported herein is the antibody as reported herein for use in treating on ocular vascular disease, preferably for use in treating macular degeneration.

The antibody as reported herein for use in inhibiting the interaction between IL-1beta and the IL-1 receptors I and II.

One aspect as reported herein is the use of the antibody as reported herein in the manufacture of a medicament.

In one embodiment the medicament is for the treatment of an ocular vascular disease, preferably for the treatment of macular degeneration.

In one embodiment the medicament is for inhibiting the interaction between IL-1beta and the IL-1 receptors I and II.

One aspect as reported herein is a method of treating an individual having on ocular vascular disease, preferably macular degeneration, comprising administering to the individual an effective amount of the antibody as reported herein.

One aspect as reported herein is a method of inhibiting the interaction between IL-1beta and the IL-1 receptors I and II in an individual comprising administering to the individual an effective amount of the antibody as reported herein to inhibiting the interaction between IL-1beta and the IL-1 receptors I and II.

DETAILED DESCRIPTION OF EMBODIMENTS OF THE INVENTION

I. Definitions

By the term "does not bind" is meant that no significant binding above background is observed when the antibody is combined with IL-1alpha or with the fibroblast growth factors as determined in an ELISA or surface plasmon resonance based method.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-IL-1beta antibody" and "an antibody that binds to IL-1beta" refer to an antibody that is capable of binding IL-1beta with sufficient affinity such that the antibody is useful as a diagnostic and/or therapeutic agent in targeting IL-1beta. In one embodiment, the extent of binding of an anti-IL-1beta antibody to an unrelated, non-IL-1beta protein is less than about 10% of the binding of the antibody to IL-1beta as measured, e.g., by ELISA or surface plasmon resonance. In certain embodiments, an antibody that binds to IL-1beta has a dissociation constant (KD) of $\leq 1$ µM, $\leq 100$ nM, $\leq 10$ nM, $\leq 1$ nM, or $\leq 0.1$ nM (e.g. $10^{-8}$M or less, e.g. from $10^{-8}$M to $10^{-10}$M, e.g., from $10^{-9}$M to $10^{-10}$ M). In certain embodiments, an anti-IL-1beta antibody binds to an epitope of IL-1beta that is conserved among IL-1beta from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that has interactions with at least the same amino acid residues as the reference antibody. These interactions are e.g. ionic interactions between charged amino acid residues or hydrophobic interactions between hydrophobic amino acid residues.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgA_1$, and $IgA_2$. The heavy chain constant domains that correspond to the different classes of immunoglobulins are called α, δ, ε, γ, and μ, respectively.

The term "immunoconjugate" denotes a covalent conjugate between an antibody and a non-antibody moiety. Such a non-antibody moiety can be a detectable label, an effector molecule or a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) or the C-terminal glycyl-lysine dipeptide (Gly446Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody", "intact antibody," and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IL-1beta antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "IL-1beta" as used herein, refers to human IL-1beta. The term encompasses "full-length," unprocessed IL-1beta as well as any form of IL-1beta that result from processing in the cell. The term also encompasses naturally occurring variants of IL-1beta, e.g., splice variants or allelic variants. The amino acid sequence of human IL-1beta is shown in SEQ ID NO: 46.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

The monoclonal humanized antibody of the invention is a humanized form of the murine antibody designated ILB1-H34 (short H34). It specifically binds to a determinant site on the IL-1beta molecule that is involved in receptor binding and proliferative activity of IL-1beta. The monoclonal humanized antibody does not bind to IL-1alpha and does not bind to acidic or basic fibroblast growth factors. Antibody ILB1-H34 blocks the binding of iodine 125 labeled IL-1beta to IL-1 receptors on mouse 3T3 fibroblasts and IL-1beta-induced thymocyte proliferation. This antibody is of the IgG1 kappa isotype. The murine HLB1-H34 antibody is produced by the ILB1-H34 murine hybridoma.

In one aspect, the invention is based, in part, on the finding for the humanization of the murine anti-human IL-1beta antibody H34 backmutations at certain positions have to be introduced in order to compensate for a loss in affinity due to the removal of a cysteine residue in the HVR-H2 which is needed in order to improve developability of the antibody and to ensure suitability for large scale production. In certain embodiments, humanized antibodies that bind to human IL-1beta are provided. Antibodies of the invention are useful, e.g., for the treatment of ocular vascular diseases, such as macular degeneration.

A. Exemplary Anti-IL-1Beta Antibodies

Herein four novel anti-human IL-1beta antibodies are provided.

The first anti-IL-1beta antibody is a novel murine anti-human IL-1beta antibody with a VH of SEQ ID NO: 09 and a VL of SEQ ID NO: 10. This antibody is termed mumAb in the following. This antibody binds to human, cynomolgus, rabbit, rat, and murine IL-1beta and inhibits the interaction between IL-1beta and the human IL-1 receptors I and II.

The antibody has the following properties:

TABLE 1

| binding to human IL-1beta | ka $[1/Ms * 10^6]$ | kd $[1/s * 10^{-4}]$ | KD $[nM]$ |
|---|---|---|---|
| mumAb (SEQ ID NO: 9 and 10) | 1.12 | 0.75 | 0.07 |

TABLE 2

| binding to cynomolgus IL-1beta | ka $[1/Ms * 10^6]$ | kd $[1/s * 10^{-4}]$ | KD $[nM]$ |
|---|---|---|---|
| mumAb (SEQ ID NO: 9 and 10) | 1.15 | 0.95 | 0.08 |

TABLE 3

| binding to murine IL-1beta | ka $[1/Ms * 10^6]$ | kd $[1/s * 10^{-4}]$ | KD $[nM]$ |
|---|---|---|---|
| mumAb (SEQ ID NO: 9 and 10) | 2.47 | 12.2 | 0.49 |
| Gevokizumab | 2.48 | 5.35 | 0.22 |

TABLE 4

| binding to rat IL-1beta | ka $[1/Ms * 10^6]$ | kd $[1/s * 10^{-4}]$ | KD $[nM]$ |
|---|---|---|---|
| mumAb (SEQ ID NO: 9 and 10) | 2.04 | 6.36 | 0.31 |
| Gevokizumab | 2.79 | 0.20 | 0.007 |

TABLE 5

| binding to rabbit IL-1beta | KD [nM] |
|---|---|
| mumAb (SEQ ID NO: 9 and 10) | 1.4 |
| Gevokizumab | n.a. |

The above data was determined by BIAcore.

TABLE 6

| origin of IL-1beta | $EC_{50}$ [ng/mL] | $EC_{50}$ (based on MWC 150 kDa) [$10^{-10}$ M] | example |
|---|---|---|---|
| human 1 | 34.02 | 2.27 | 4 variant 1 |
| human 2 | 15.16 | 1.01 | 4 variant 2 |
| murine | 23.07 | 1.54 | 6 |
| cynomolgus | 21.27 | 1.42 | 5 |

The above data was determined by ELISA.
Inhibition of binding of IL-1beta to IL-1 receptor I and II:

TABLE 7

| | $IC_{50}$ [ng/mL] | $IC_{50}$ (based on MWC 150 kDa) [$10^{-9}$M] | example |
|---|---|---|---|
| IL-1beta receptor I | 230.9 | 1.54 | 7 |
| IL-1beta receptor II | 132.4 | 0.88 | 8 |

The above data was determined by ELISA.

In a stimulation experiment it could be shown that the murine antibodies as reported herein can inhibit ICAM-1 expression upon IL-1β stimulation of A549 cells (see Table 8 below).

TABLE 8

| antibody | $IC_{50}$ [nM] |
|---|---|
| mumAb | 0.7 |

In the following Table the $IC_{50}$ value for inhibition of ICAM-1 expression upon IL-1beta stimulation of HUVEC cells is shown.

TABLE 9

| antibody | $IC_{50}$ [nM] |
|---|---|
| mumAb | 16.50 |

In stimulation experiments it could be shown that the humanized antibodies as reported herein reduce IL-6 expression upon IL-1beta stimulation of A549 cells (see Table 10 below).

TABLE 10

| antibody | $EC_{50}$ [nM] |
|---|---|
| mumAb | 1.09 |

In addition, the murine antibody showed stability in stress tests. The binding activity has been determined using surface plasmon resonance (see Table 11 below).

TABLE 11

| | relative binding activity | |
|---|---|---|
| antibody | 2 weeks at 37° C. pH 7.5 | 2 weeks at 40° C. pH 6.0 |
| mumAb | 103% | 102% |

100% = sample stored at −80° C.

The same stability can be seen when the high molecular weight content is determined (see Table 12 below).

TABLE 12

| | high molecular weight fraction | | |
|---|---|---|---|
| antibody | start | 2 weeks at 37° C. pH 7.4 | 2 weeks at 40° C. pH 6.0 |
| mumAb | 0.97% | 1.24% | 1.00% |

The same stability can be seen in the CE-SDS analysis (see Table 13 below).

TABLE 13

| | relative area % | | |
|---|---|---|---|
| antibody | start | 2 weeks at 37° C. pH 7.4 | 2 weeks at 40° C. pH 6.0 |
| mumAb | 91.9% | 86.5% | 90.0% |

The thermal stability of the murine antibody has been evaluated by determining the aggregation onset temperature (Tagg) and the melting temperature (Tm) (see Table 14 below).

TABLE 14

| antibody | Tagg [° C.] | Tm [° C.] |
|---|---|---|
| mumAb | approx. 60 | approx. 64 |

The other three antibodies are humanized variants of the murine anti-IL1-beta antibody H34: huH34-1 (SEQ ID NO: 3, 6, and 18 to 24), huH34-2 (SEQ ID NO: 4, 6 and 25 to 31) and huH34-3 (SEQ ID NO: 5, 6 and 32 to 38).

Herein is reported a humanized anti-IL1beta antibody. This antibody is derived from the murine anti-IL1beta antibody H34.

One aspect as reported herein is a monoclonal antibody that is a humanized variant of the murine anti-IL-1beta antibody H34. This antibody is reported in U.S. Pat. No. 4,935,343.

Based upon the amino acid sequence of the murine H34 antibody (SEQ ID NO: 01 and 02), a corresponding humanized anti-IL-1β antibody was generated (huH34-2). The humanized variant VH is based on the human VBase_VH1_1 and the J-element of the human IGHJ4-01-3 germline (huH34-1). In order to restore affinity one back-mutation was introduced at position 48 of framework region 2 (M48I). In framework region 3, 4 positions were backmutated: V67A, M69F, R71V and A93V. In addition, the cysteine in position 52a of HVR-H2 was replaced by a serine. For VL, the humanized variant is based on the human IMGT_hVK_3_11 germline with an IGKJ2-01 J-element. One backmutation was introduced at positions 36 of framework region 2 (Y36S). The amino acid sequence of the humanized VH is shown in SEQ ID NO: 04 and the amino acid sequence of the humanized VL is shown in SEQ ID NO: 06.

Murine anti-IL-1beta antibody H34 contains a cysteine in HVR-H2 (C52a, Kabat numbering) that needs to be removed for development as a therapeutic candidate that can be produced at large scale. Removing this Cys by a C52aS mutation in the murine antibody results in a reduced affinity for IL-1beta by a factor of about 6 to 7 (see Tables 15 and 16 below).

TABLE 15

|  | ka<br>[1/Ms * $10^6$] | kd<br>[1/s * $10^{-4}$] | KD<br>[nM] |
|---|---|---|---|
| binding to human IL-1beta antibody |  |  |  |
| H34 | 1.85 | 1.27 | 0.07 |
| H34 + C52aS mutations | 1.60 | 6.45 | 0.40 |
| binding to cynomolgus IL-1beta antibody |  |  |  |
| H34 | 1.99 | 0.98 | 0.05 |
| H34 + C52aS mutations | 1.43 | 7.28 | 0.51 |

The above data was determined by BIAcore.

For the humanized version of H34 (huH34-2) the loss of affinity upon C52aS mutation is compensated and this antibody has a comparable affinity (and comparable functional potency in cellular assays) as the murine parental antibody H34.

This compensation effect is accountable to the germline sequence that was chosen for humanization and the choice of backmutations within framework IGHJ4-01-3 and IMGT_hVK_3_11. An additional variant was designed based on the same human germline for VH (IGHJ4-01-3) and VL (IMGT_hVK_3_11), respectively. Backmutations described for huH34-2 were omitted from the VH and VL sequence (SEQ ID NO: 7 and 8).

TABLE 16

|  | ka<br>[1/Ms * $10^6$] | kd<br>[1/s * $10^{-4}$] | KD<br>[nM] |
|---|---|---|---|
| binding to human IL-1beta antibody |  |  |  |
| H34 | 1.85 | 1.27 | 0.07 |
| H34 + C52aS mutations | 1.60 | 6.45 | 0.40 |
| huH34-1 | 1.49 | 15.1 | 1.02 |
| huH34-2 | 1.93 | 1.10 | 0.06 |
| huH34-2 FAB | 1.81 | 1.11 | 0.06 |
| huH34-3 | 1.97 | 3.02 | 0.15 |
| Gevokizumab | 3.01 | 0.52 | 0.02 |
| Canakinumab | 2.78 | 0.52 | 0.02 |
| binding to cynomolgus IL-1beta antibody |  |  |  |
| H34 | 1.99 | 0.98 | 0.05 |
| H34 + C52aS mutations | 1.43 | 7.28 | 0.51 |
| huH34-1 | 1.61 | 21.2 | 1.31 |
| huH34-2 | 2.20 | 1.18 | 0.05 |
| huH34-3 | 2.21 | 4.91 | 0.22 |

TABLE 16-continued

|  | ka<br>[1/Ms * $10^6$] | kd<br>[1/s * $10^{-4}$] | KD<br>[nM] |
|---|---|---|---|
| Gevokizumab | 3.21 | 0.67 | 0.02 |
| Canakinumab | 2.15 | 284 | 13.2 |

The above data was determined by BIAcore.

In one embodiment the humanized anti-IL-1beta antibody binds to human and cynomolgus IL-1beta.

In the presence of human IL-1beta the binding signal in a surface plasmon resonance experiment using immobilized IL-1 receptor I increased for Gevokizumab. Thus, antibody-bound IL-1b still binds to IL-1 receptor I. Therefore, the mode of action for Gevokizumab is allosteric inhibition of IL-1RAc binding (allosteric antibody).

For Canakinumab, H34 and mumAb IL-1beta binding to IL-1 receptor I is prevented after antibody binding. Thus, mode of action is receptor blocking for Canakinumab, H34 and mumAb (competitive antibody).

TABLE 17

| antibody | $IC_{50}$ in the presence of @ 10 nM IL-1beta<br>[nM] |
|---|---|
| Canakinumab | 1.6 |
| mumAb | 2.5 |
| H34 | 3.5 |

In stimulation experiments it could be shown that the humanized antibodies as reported herein have the same activity as the murine parental antibody. In the following Table the $IC_{50}$ values for inhibition of ICAM-1 expression upon IL-1beta stimulation of A549 cells are shown for different antibodies.

TABLE 18

| antibody | $IC_{50}$<br>[nM] |
|---|---|
| H34 | 0.18 |
| huH34-1 | >7 |
| huH34-2 | 0.23 |
| huH34-3 | 2.23 |
| Gevokizumab | 0.94 |
| Canakinumab | 0.31 |

In the following Table the $IC_{50}$ value for inhibition of ICAM-1 expression upon IL-1beta stimulation of HUVEC cells is shown.

TABLE 19

| antibody | $IC_{50}$<br>[nM] |
|---|---|
| H34 | 0.24 |
| huH34-2 | 0.30 |
| Canakinumab | 9.02 |

In stimulation experiments it could be shown that the humanized antibodies as reported herein reduce IL-6 expression upon IL-1beta stimulation of A549 cells (see Table below).

TABLE 20

| antibody | EC$_{50}$ [nM] |
|---|---|
| huH34-1 | 5.52 |
| huH34-2 | 0.11 |
| huH34-3 | 1.09 |
| Gevokizumab | 0.11 |
| Canakinumab | 0.12 |

In proliferation inhibition experiments it could be shown that the humanized antibody as reported herein inhibits proliferation of D10 cells (see Table 21 below).

TABLE 21

| antibody | IC$_{50}$ [nM] |
|---|---|
| huH34-2 | 0.83 |
| Gevokizumab | 3.36 |
| Canakinumab | 1.99 |

In the following Table the IC$_{50}$ values for inhibition of TNFalpha expression upon MSU stimulation of THP1 cells are shown for different antibodies.

TABLE 22

| antibody | IC$_{50}$ [nM] |
|---|---|
| H34 | 0.43 |
| huH34-2 | 2.38 |
| Canakinumab | 0.41 |

In addition, the humanized antibodies show improved stability compared to the murine H34 parent antibody in stress tests. The binding activity has been determined using surface plasmon resonance (see Table 23 below).

TABLE 23

| | relative binding activity | |
|---|---|---|
| antibody | 2 weeks at 37° C. pH 7.4 | 2 weeks at 40° C. pH 6.0 |
| H34 | 70% | 101% |
| huH34-1 | 96% | 99% |
| huH34-2 | 94% | 99% |
| huH34-3 | 96% | 100% |

100% = sample stored at −80° C.

The same stability can be seen when the high molecular weight content is determined (see Table 24 below).

TABLE 24

| | | high molecular weight fraction | |
|---|---|---|---|
| antibody | start | 2 weeks at 37° C. pH 7.4 | 2 weeks at 40° C. pH 6.0 |
| huH34-1 | 4.57% | 4.13% | 4.39% |
| huH34-2 | 0.21% | 0.15% | 0.13% |
| huH34-3 | 0.19% | 0.17% | 0.13% |

The same stability can be seen in the CE-SDS analysis (see Table 25 below).

TABLE 25

| | | relative area % | |
|---|---|---|---|
| antibody | start | 2 weeks at 37° C. pH 7.4 | 2 weeks at 40° C. pH 6.0 |
| huH34-1 | 96.1% | 92.9% | 93.8% |
| huH34-2 | 96.4% | 92.5% | 95.2% |
| huH34-3 | 96.0% | 92.1% | 95.1% |

The thermal stability of the different humanized antibodies has been evaluated by determining the aggregation onset temperature (Tagg) and the melting temperature (Tm) (see Table 26 below).

TABLE 26

| antibody | Tagg [° C.] | Tm [° C.] |
|---|---|---|
| huH34-1 | 61.5 | 69.1 |
| huH34-2 | 63.0 | 72.0 |
| huH34-3 | 63.0 | 70.6 |

The high-resolution crystal structure of the huH34-2 Fab-fragment bound to human beta showed detailed information on the functional epitope of this antibody. The structure was compared to the structure of the ternary IL-1b signaling complex (human IL-1b bound to the IL-1 receptor 1, IL-1R1, and the IL-1 accessory protein, IL-1RAcP, PDB code 4DEP). It has been found that the epitope of huH34 overlaps with the interaction sites of both IL-1R1 and IL-1RAcP. Thus, the antibody blocks the formation of the IL-1 beta signaling complex at the first step of its assembly, which is the association of IL-1 beta and the IL-1R1.

Antibody 0031 is a bispecific anti-ANG2/IL-1beta antibody comprising as the IL-1beta binding specificity the VH and VL domain of huH34-2.

Antibody 0032 is a bispecific anti-VEGF/IL-1beta antibody comprising as the IL-1beta binding specificity the VH and VL domain of huH34-2.

For the determination of the kinetic binding values the assay as reported in Example 26 was used.

TABLE 27

| ANG2 | ka [1/Ms] | kd [1/s] | KD* [nM] | t½ [s] |
|---|---|---|---|---|
| antibody-0031 | 1.45E+05 | 1.15E−03 | 8 | 604 |

TABLE 28

| VEGF | ka [1/Ms] | kd [1/s] | KD* [nM] | t½ [s] |
|---|---|---|---|---|
| antibody-0032 | 2.77E+04 | <1E−06 | <0.1 | — |

TABLE 29

| IL-1beta | ka [1/Ms] | kd [1/s] | KD* [nM] | t½ [s] |
|---|---|---|---|---|
| huH34-2 bivalent | 2.43E+06 | 1.15E−04 | 0.05 | 101 |
| antibody-0031 | 2.56E+06 | 3.02E−04 | 0.12 | 38 |
| antibody-0032 | 2.49E+06 | 3.05E−04 | 0.12 | 38 |

It has been shown by SPR analysis that all bispecific antibodies have the property of binding to both its antigens simultaneously.

In an ANG2 specific pTie2-ELISA the antibody 0031, is 6 times more active than the anti-ANG2/VEGF antibody reported in WO 2014/09465.

In one embodiment the humanized anti-IL-1beta antibody binds to human and cynomolgus IL-1beta.

In the following Table the $IC_{50}$ value for inhibition of ICAM-1 expression upon IL-1beta stimulation of A549 cells is shown.

TABLE 30

| antibody | $IC_{50}$ [ng/mL] |
|---|---|
| antibody 0031 | 103.9 |
| Gevokizumab | 204.4 |

In the following Table the $IC_{50}$ value for inhibition of ICAM-1 expression upon IL-1beta stimulation of HUVEC cells is shown.

TABLE 31

| antibody | $IC_{50}$ [ng/mL] |
|---|---|
| huH34-2 | 1.2-0.9 |
| huH34-2 Fab | 1.1-2.5 |
| antibody 0031 | 2.0-5.5 |
| antibody 0032 | 3.5-6.3 |

In stimulation experiments it could be shown that the humanized antibodies as reported herein reduce IL-6 expression upon IL-1beta stimulation of A549 cells (see Table 32 below).

TABLE 32

| antibody | $EC_{50}$ [ng/mL] |
|---|---|
| antibody 0031 | 17.0 |
| antibody 0032 | 38.7 |
| Gevokizumab | 62.0 |
| Canakinumab | 86.4 |

The thermal stability of the different bispecific antibodies has been evaluated by determining the aggregation onset temperature (Tagg) and the melting temperature (Tm) (see Table 33 below).

TABLE 33

| antibody | Tagg [° C.] | Tm [° C.] |
|---|---|---|
| 0031 | 61 | 67.5 |
| 0032 | 55 | 62.5 |

Antibody huH34-2 is described with the sequences of SEQ ID NO: 04, 06 and 25 to 31 (binding sites, HVRs, VH, VL). The bispecific formats of antibody huH34-2 are described in sequences SEQ ID NO: 49 to 52 and 57 to 60. All of these sequences constitute alone d in combination aspects of the current invention.

One aspect as reported herein is a humanized anti-human IL-1beta antibody comprising (a) a HVR-H1 comprising the amino acid sequence of SEQ ID NO: 25; (b) a HVR-H2 comprising the amino acid sequence of SEQ ID NO: 27; and (c) a HVR-H3 comprising the amino acid sequence of SEQ ID NO: 28. In one embodiment the antibody further comprises (d) a HVR-L1 comprising the amino acid sequence of SEQ ID NO: 29; (e) a HVR-L2 comprising the amino acid sequence of SEQ ID NO: 30; and (f) a HVR-L3 comprising the amino acid sequence of SEQ ID NO: 31. In one preferred embodiment the humanized anti-human IL-1beta antibody as reported herein specifically binds to human and cynomolgus IL-1beta and comprises (a) a HVR-H1 comprising the amino acid sequence of SEQ ID NO: 25, (b) a HVR-H2 comprising the amino acid sequence of SEQ ID NO: 27, (c) a HVR-H3 comprising the amino acid sequence of SEQ ID NO: 28, (d) a HVR-L1 comprising the amino acid sequence of SEQ ID NO: 29, (e) a HVR-L2 comprising the amino acid sequence of SEQ ID NO: 30, and (f) a HVR-L3 comprising the amino acid sequence of SEQ ID NO: 31. In one preferred embodiment the humanized anti-human IL-1beta antibody as reported herein has a heavy chain variable domain that has the amino acid sequence of SEQ ID NO: 04 and a light chain variable domain that has the amino acid sequence of SEQ ID NO: 06. In one preferred embodiment the humanized anti-human IL-1beta antibody as reported herein is a bispecific antibody.

One aspect as reported herein is a humanized anti-human IL-1beta antibody comprising (a) a HVR-H1 comprising the amino acid sequence of SEQ ID NO: 25; (b) a HVR-H2 comprising the amino acid sequence of SEQ ID NO: 26; and (c) a HVR-H3 comprising the amino acid sequence of SEQ ID NO: 28. In one embodiment the antibody further comprises (d) a HVR-L1 comprising the amino acid sequence of SEQ ID NO: 29; (e) a HVR-L2 comprising the amino acid sequence of SEQ ID NO: 30; and (f) a HVR-L3 comprising the amino acid sequence of SEQ ID NO: 31.

One aspect as reported herein is an anti-human IL-1beta antibody comprising (a) a HVR-H1 comprising the amino acid sequence of SEQ ID NO: 39; (b) a HVR-H2 comprising the amino acid sequence of SEQ ID NO: 41; and (c) a HVR-H3 comprising the amino acid sequence of SEQ ID NO: 42. In one embodiment the antibody further comprises (d) a HVR-L1 comprising the amino acid sequence of SEQ ID NO: 43; (e) a HVR-L2 comprising the amino acid sequence of SEQ ID NO: 44; and (f) a HVR-L3 comprising the amino acid sequence of SEQ ID NO: 45.

In one aspect, the invention provides an anti-IL-1beta antibody comprising at least one, two, three, four, five, or six HVRs selected from (a) a HVR-H1 comprising the amino acid sequence of SEQ ID NO: 25; (b) a HVR-H2 comprising the amino acid sequence of SEQ ID NO: 27; (c) a HVR-H3 comprising the amino acid sequence of SEQ ID NO: 28; (d) a HVR-L1 comprising the amino acid sequence of SEQ ID NO: 29; (e) a HVR-L2 comprising the amino acid sequence of SEQ ID NO: 30; and (f) a HVR-L3 comprising the amino acid sequence of SEQ ID NO: 31.

In one aspect, the invention provides an antibody comprising at least one, at least two, or all three VH HVR sequences selected from (a) a HVR-H1 comprising the amino acid sequence of SEQ ID NO: 25; (b) a HVR-H2 comprising the amino acid sequence of SEQ ID NO: 27; and (c) a HVR-H3 comprising the amino acid sequence of SEQ ID NO: 28. In one embodiment, the antibody comprises a HVR-H3 comprising the amino acid sequence of SEQ ID NO: 28. In another embodiment, the antibody comprises a HVR-H3 comprising the amino acid sequence of SEQ ID NO: 28 and a HVR-L3 comprising the amino acid sequence of SEQ ID NO: 31. In a further embodiment, the antibody comprises a HVR-H3 comprising the amino acid sequence of SEQ ID NO: 28, a HVR-L3 comprising the amino acid sequence of SEQ ID NO: 31, and a HVR-H2 comprising the amino acid sequence of SEQ ID NO: 27. In a further embodiment, the antibody comprises (a) a HVR-H1 comprising the amino acid sequence of SEQ ID NO: 25; (b) a HVR-H2 comprising the amino acid sequence of SEQ ID NO: 26; and (c) a HVR-H3 comprising the amino acid sequence of SEQ ID NO: 28.

In another aspect, the invention provides an antibody comprising at least one, at least two, or all three VL HVR sequences selected from (a) a HVR-L1 comprising the amino acid sequence of SEQ ID NO: 29; (b) a HVR-L2 comprising the amino acid sequence of SEQ ID NO: 30; and (c) a HVR-L3 comprising the amino acid sequence of SEQ ID NO: 31. In one embodiment, the antibody comprises (a) a HVR-L1 comprising the amino acid sequence of SEQ ID NO: 29; (b) a HVR-L2 comprising the amino acid sequence of SEQ ID NO: 30; and (c) a HVR-L3 comprising the amino acid sequence of SEQ ID NO: 31.

In another aspect, an antibody of the invention comprises (a) a VH domain comprising at least one, at least two, or all three VH HVR sequences selected from (i) a HVR-H1 comprising the amino acid sequence of SEQ ID NO: 25, (ii) a HVR-H2 comprising the amino acid sequence of SEQ ID NO: 27, and (iii) a HVR-H3 comprising an amino acid sequence selected from SEQ ID NO: 28; and (b) a VL domain comprising at least one, at least two, or all three VL HVR sequences selected from (i) a HVR-L1 comprising the amino acid sequence of SEQ ID NO: 29, (ii) a HVR-L2 comprising the amino acid sequence of SEQ ID NO: 30, and (c) a HVR-L3 comprising the amino acid sequence of SEQ ID NO: 31.

In another aspect, the invention provides an antibody comprising (a) a HVR-H1 comprising the amino acid sequence of SEQ ID NO: 25; (b) a HVR-H2 comprising the amino acid sequence of SEQ ID NO: 27; (c) a HVR-H3 comprising the amino acid sequence of SEQ ID NO: 28; (d) a HVR-L1 comprising the amino acid sequence of SEQ ID NO: 29; (e) a HVR-L2 comprising the amino acid sequence of SEQ ID NO: 30; and (f) a HVR-L3 comprising an amino acid sequence selected from SEQ ID NO: 31.

In another aspect, an anti-IL-1beta antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 04. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-1beta antibody comprising that sequence retains the ability to bind to IL-1beta. In certain embodiments, a total of 1 to 10 amino acids have been substituted, inserted and/or deleted in SEQ ID NO: 04. In certain embodiments, substitutions, insertions, or deletions occur in regions outside the HVRs (i.e., in the FRs). Optionally, the anti-IL-1beta antibody comprises the VH sequence in SEQ ID NO: 04, including post-translational modifications of that sequence. In a particular embodiment, the VH comprises one, two or three HVRs selected from: (a) HVR-H1 comprising the amino acid sequence of SEQ ID NO: 25, (b) HVR-H2 comprising the amino acid sequence of SEQ ID NO: 27, and (c) HVR-H3 comprising the amino acid sequence of SEQ ID NO: 28.

In another aspect, an anti-IL-1beta antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 06. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-1beta antibody comprising that sequence retains the ability to bind to IL-1beta. In certain embodiments, a total of 1 to 10 amino acids have been substituted, inserted and/or deleted in SEQ ID NO: 06. In certain embodiments, the substitutions, insertions, or deletions occur in regions outside the HVRs (i.e., in the FRs). Optionally, the anti-IL-1beta antibody comprises the VL sequence in SEQ ID NO: 06, including post-translational modifications of that sequence. In a particular embodiment, the VL comprises one, two or three HVRs selected from (a) HVR-L1 comprising the amino acid sequence of SEQ ID NO: 29; (b) HVR-L2 comprising the amino acid sequence of SEQ ID NO: 30; and (c) HVR-L3 comprising the amino acid sequence of SEQ ID NO: 31.

In another aspect, an anti-IL-1beta antibody is provided, wherein the antibody comprises a VH as in any of the embodiments provided above, and a VL as in any of the embodiments provided above. In one embodiment, the antibody comprises the VH and VL sequences in SEQ ID NO: 04 and SEQ ID NO: 06, respectively, including post-translational modifications of those sequences.

In a further aspect of the invention, an anti-IL-1beta antibody according to any of the above embodiments is a monoclonal antibody. In one embodiment, an anti-IL-1beta antibody is an antibody fragment, e.g., an Fv, Fab, Fab', scFv, diabody, or F(ab')$_2$ fragment. In another embodiment, the antibody is a full length antibody, e.g., an intact IgG1 antibody or other antibody class or isotype as defined herein.

In one embodiment of all aspects as reported herein the anti-IL-1beta antibody is an effector silent anti-IL-1beta antibody. In one embodiment of all aspects as reported herein the anti-IL-1beta antibody is an effector silent anti-IL-1beta antibody and does not bind to human FcRn. In one embodiment of all aspects as reported herein is the anti-IL-1beta antibody of the human subclass IgG1 and has the mutations L234A, L235A, P329G, I253A, H310A and H434A in both heavy chains (numbering according to the Kabat index).

In one embodiment of all aspects as reported herein the anti-IL-1beta antibody is a bispecific antibody.

One aspect as reported herein is a bivalent, bispecific antibody comprising
a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other,
wherein the first antigen or the second antigen is human IL-1beta.

The antibody under a) does not contain a modification as reported under b) and the heavy chain and the light chain under a) are isolated chains.

In the antibody under b)
within the light chain
the variable light chain domain VL is replaced by the variable heavy chain domain VH of said antibody, and
within the heavy chain
the variable heavy chain domain VH is replaced by the variable light chain domain VL of said antibody.

In one embodiment
i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid, or ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other, wherein the first antigen or the second antigen is human IL-1beta.

The antibody under a) does not contain a modification as reported under b) and the heavy chain and the light chain and a) are isolated chains.

In the antibody under b)

within the light chain the variable light chain domain VL is replaced by the variable heavy chain domain VH of said antibody, and the constant light chain domain CL is replaced by the constant heavy chain domain CH1 of said antibody;

and within the heavy chain the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising a) a first light chain and a first heavy chain of an antibody specifically binding to a first antigen, and b) a second light chain and a second heavy chain of an antibody specifically binding to a second antigen, wherein the constant domains CL and CH1 of the second light chain and the second heavy chain are replaced by each other, wherein the first antigen or the second antigen is human IL-1beta.

The antibody under a) does not contain a modification as reported under b) and the heavy chain and the light chain under a) are isolated chains.

In the antibody under b)

within the light chain the constant light chain domain CL is replaced by the constant heavy chain domain CH1 of said antibody;

and within the heavy chain the constant heavy chain domain CH1 is replaced by the constant light chain domain CL of said antibody.

One aspect as reported herein is a multispecific antibody comprising a) a full length antibody specifically binding to a first antigen and consisting of two antibody heavy chains and two antibody light chains, and b) one, two, three or four single chain Fab fragments specifically binding to one to four further antigens (i.e. a second and/or third and/or fourth and/or fifth antigen, preferably specifically binding to one further antigen, i.e. a second antigen), wherein said single chain Fab fragments under b) are fused to said full length antibody under a) via a peptidic linker at the C- or N-terminus of the heavy or light chain of said full length antibody, wherein the first antigen or one of the further antigens is human IL-1beta.

In one embodiment one or two identical single chain Fab fragments binding to a second antigen are fused to said full length antibody via a peptidic linker at the C-terminus of the heavy or light chains of said full length antibody.

In one embodiment one or two identical single chain Fab fragments binding to a second antigen are fused to said full length antibody via a peptidic linker at the C-terminus of the heavy chains of said full length antibody.

In one embodiment one or two identical single chain Fab fragments binding to a second antigen are fused to said full length antibody via a peptidic linker at the C-terminus of the light chains of said full length antibody.

In one embodiment two identical single chain Fab fragments binding to a second antigen are fused to said full length antibody via a peptidic linker at the C-terminus of each heavy or light chain of said full length antibody.

In one embodiment two identical single chain Fab fragments binding to a second antigen are fused to said full length antibody via a peptidic linker at the C-terminus of each heavy chain of said full length antibody.

In one embodiment two identical single chain Fab fragments binding to a second antigen are fused to said full length antibody via a peptidic linker at the C-terminus of each light chain of said full length antibody.

One aspect as reported herein is a trivalent, bispecific antibody comprising
  a) a full length antibody specifically binding to a first antigen and consisting of two antibody heavy chains and two antibody light chains,
  b) a first polypeptide consisting of
    ba) an antibody heavy chain variable domain (VH), or
    bb) an antibody heavy chain variable domain (VH) and an antibody constant domain 1 (CH1),
  wherein said first polypeptide is fused with the N-terminus of its VH domain via a peptidic linker to the C-terminus of one of the two heavy chains of said full length antibody,
  c) a second polypeptide consisting of
    ca) an antibody light chain variable domain (VL), or
    cb) an antibody light chain variable domain (VL) and an antibody light chain constant domain (CL),
  wherein said second polypeptide is fused with the N-terminus of the VL domain via a peptidic linker to the C-terminus of the other of the two heavy chains of said full length antibody,
  and
  wherein the antibody heavy chain variable domain (VH) of the first polypeptide and the antibody light chain variable domain (VL) of the second polypeptide together form an antigen-binding site specifically binding to a second antigen,
  and
  wherein the first antigen or the second antigen is human IL-1beta.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
  i) heavy chain variable domain position 44 to light chain variable domain position 100, or
  ii) heavy chain variable domain position 105 to light chain variable domain position 43, or
  iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43. (numbering always according to EU index of Kabat) In one embodiment a trivalent, bispecific antibody without said optional disulfide stabilization between the variable domains VH and VL of the single chain Fab fragments is preferred.

One aspect as reported herein is a trispecific or tetraspecific antibody, comprising
  a) a first light chain and a first heavy chain of a full length antibody which specifically binds to a first antigen, and
  b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
  c) wherein one to four antigen binding peptides which specifically bind to one or two further antigens (i.e. to a third and/or fourth antigen) are fused via a peptidic linker to the C- or N-terminus of the light chains or heavy chains of a) and/or b),
  wherein the first antigen or the second antigen or one of the further antigens is human IL-1beta.

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising a) two light chains and two heavy chains of an antibody, which specifically bind to a first antigen (and comprise two Fab fragments),
b) two additional Fab fragments of an antibody, which specifically bind to a second antigen, wherein said additional Fab fragments are fused both via a peptidic linker either to the C- or N-termini of the heavy chains of a),
and
wherein in the Fab fragments the following modifications were performed
  i) in both Fab fragments of a), or in both Fab fragments of b), the variable domains VL and VH are replaced by each other, and/or the constant domains CL and CH1 are replaced by each other,
  or
  ii) in both Fab fragments of a) the variable domains VL and VH are replaced by each other, and the constant domains CL and CH1 are replaced by each other,
  and
    in both Fab fragments of b) the variable domains VL and VH are replaced by each other, or the constant domains CL and CH1 are replaced by each other,
  or
  iii) in both Fab fragments of a) the variable domains VL and VH are replaced by each other, or the constant domains CL and CH1 are replaced by each other,
  and
    in both Fab fragments of b) the variable domains VL and VH are replaced by each other, and the constant domains CL and CH1 are replaced by each other,
  or
  iv) in both Fab fragments of a) the variable domains VL and VH are replaced by each other, and in both Fab fragments of b) the constant domains CL and CH1 are replaced by each other,
  or
  v) in both Fab fragments of a) the constant domains CL and CH1 are replaced by each other, and in both Fab fragments of b) the variable domains VL and VH are replaced by each other,
wherein the first antigen or the second antigen is human IL-1beta.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
  i) in both Fab fragments of a), or in both Fab fragments of b), the variable domains VL and VH are replaced by each other,
  and/or
    the constant domains CL and CH1 are replaced by each other.

In one embodiment in the Fab fragments the following modifications are performed:
  i) in both Fab fragments of a) the variable domains VL and VH are replaced by each other,
  and/or
    the constant domains CL and CH1 are replaced by each other.

In one embodiment in the Fab fragments the following modifications are performed:
  i) in both Fab fragments of a) the constant domains CL and CH1 are replaced by each other.

In one embodiment in the Fab fragments the following modifications are performed:
  i) in both Fab fragments of b) the variable domains VL and VH are replaced by each other,
  and/or
    the constant domains CL and CH1 are replaced by each other.

In one embodiment in the Fab fragments the following modifications are performed:
  i) in both Fab fragments of b) the constant domains CL and CH1 are replaced by each other.

One aspect as reported herein is a bispecific, tetravalent antibody comprising:
  a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
  b) two light chains of said first antibody of a),
  c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
  d) two (modified) light chains of said second antibody of c), each comprising a CL-CH1 domain pair,
wherein the first antigen or the second antigen is human IL-1beta.

One aspect as reported herein is a bispecific antibody comprising
  a) the heavy chain and the light chain of a first full length antibody that specifically binds to a first antigen, and
  b) the heavy chain and the light chain of a second full length antibody that specifically binds to a second antigen, wherein the N-terminus of the heavy chain is connected to the C-terminus of the light chain via a peptidic linker,
wherein the first antigen or the second antigen is human IL-1beta.

The antibody under a) does not contain a modification as reported under b) and the heavy chain and the light chain are isolated chains.

One aspect as reported herein is a bispecific antibody comprising
  a) a full length antibody specifically binding to a first antigen and consisting of two antibody heavy chains and two antibody light chains, and
  b) an Fv fragment specifically binding to a second antigen comprising a $VH^2$ domain and a $VL^2$ domain, wherein both domains are connected to each other via a disulfide bridge,
  wherein only either the $VH^2$ domain or the $VL^2$ domain is fused via a peptidic linker to the heavy or light chain of the full length antibody specifically binding to a first antigen,
wherein the first antigen or the second antigen is human IL-1beta.

In the bispecific the heavy chains and the light chains under a) are isolated chains.

In one embodiment the other of the VH² domain or the VL² domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one embodiment of all aspects the antibody as reported herein is a multispecific antibody, which requires heterodimerization of at least two heavy chain polypeptides, and wherein the antibody specifically binds to human IL-1beta and a second non-human IL-1beta antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference.

Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in a multispecific antibody according to the invention, which comprises a "non-crossed Fab region" derived from a first antibody, which specifically binds to a first antigen, and a "crossed Fab region" derived from a second antibody, which specifically binds to a second antigen, in combination with the particular amino acid substitutions described above for the invention.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multispecific antibody as reported herein the positively charged amino acid is selected from K, R and H, and the negatively charged amino acid is selected from E or D.

In one embodiment of said CH3(+/−)-engineered multispecific antibody as reported herein the positively charged amino acid is selected from K and R, and the negatively charged amino acid is selected from E or D.

In one embodiment of said CH3(+/−)-engineered multispecific antibody as reported herein the positively charged amino acid is K, and the negatively charged amino acid is E.

In one embodiment of said CH3(+/−)-engineered multispecific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO 2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO 2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another embodiment of said multispecific antibody as reported herein (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment of the invention the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

In a further aspect, an anti-IL-1beta antibody according to any of the above embodiments may incorporate any of the features, singly or in combination, as described in Sections 1-5 below.

1. Antibody Affinity

In certain embodiments, an antibody provided herein has a dissociation constant (KD) of ≤1 μM, ≤100 nM, ≤10 nM, ≤1 nM, or ≤0.1 nM (e.g. $10^{-8}$M or less, e.g. from $10^{-8}$M to $10^{-10}$ M, e.g., from $10^{-9}$M to $10^{-10}$ M).

Methods for the determination of the KD value are outlined in the Examples below.

When using a BIACORE® surface plasmon resonance assay the KD value can be measured alternatively as follows: An assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_a$) and dissociation rates ($k_d$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio $k_d/k_a$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the association-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. No. 5,571,894 and U.S. Pat. No. 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and U.S. Pat. No. 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for IL-1beta and the other is for any other antigen. In certain embodiments, bispecific antibodies may bind to two different epitopes of IL-1beta. Bispecific antibodies may also be used to localize cytotoxic agents to cells which express IL-1beta. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to IL-1beta as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 34

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

Amino acids may be grouped according to common side-chain properties:
(1) hydrophobic: norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch, J. V. and Kinet, J.

P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371, 826).

See also Duncan, A. R. and Winter, G., Nature 322 (1988) 738-740; U.S. Pat. No. 5,648,260; U.S. Pat. No. 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-IL-1beta antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-IL-1beta antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL-1beta antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-IL-1beta antibodies provided herein may be identified, screened for, or characterized for their physical/chemical properties and/or biological activities by various assays known in the art. Exemplary assays are reported in the Examples.

D. Immunoconjugates

The invention also provides immunoconjugates comprising an anti-IL-1beta antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and U.S. Pat. No. 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl sulfone)benzoate) which are commercially available (e.g., from Pierce Biotechnology, Inc., Rockford, Ill., U.S.A.).

E. Methods and Compositions for Diagnostics and Detection

In certain embodiments, any of the anti-IL-1beta antibodies provided herein is useful for detecting the presence of IL-1beta in a biological sample. The term "detecting" as used herein encompasses quantitative or qualitative detection.

In one embodiment, an anti-IL-1beta antibody for use in a method of diagnosis or detection is provided. In a further aspect, a method of detecting the presence of IL-1beta in a biological sample is provided. In certain embodiments, the method comprises contacting the biological sample with an anti-IL-1beta antibody as described herein under conditions permissive for binding of the anti-IL-1beta antibody to IL-1beta, and detecting whether a complex is formed between the anti-IL-1beta antibody and IL-1beta. Such method may be an in vitro or in vivo method. In one embodiment, an anti-IL-1beta antibody is used to select subjects eligible for therapy with an anti-IL-1beta antibody, e.g. where IL-1beta is a biomarker for selection of patients.

In certain embodiments, labeled anti-IL-1beta antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-IL-1beta antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an anti-ANG2 antibody or an anti-VEGF antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16$^{th}$ edition, Osol, A. (ed.) (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-IL-1beta antibodies provided herein may be used in therapeutic methods.

In one aspect, an anti-IL-1beta antibody for use as a medicament is provided. In further aspects, an anti-IL-1beta antibody for use in treating an ocular vascular disease, preferably macular degeneration, is provided. In certain embodiments, an anti-IL-1beta antibody for use in a method of treatment is provided. In certain embodiments, the invention provides an anti-IL-1beta antibody for use in a method of treating an individual having an ocular vascular disease, preferably macular degeneration, comprising administering to the individual an effective amount of the anti-IL-1beta antibody. In one such embodiment, the method further comprises administering to the individual an effective amount of at least one additional therapeutic agent, e.g., as described below. In further embodiments, the invention provides an anti-IL-1beta antibody for use in inhibiting angiogenesis. In certain embodiments, the invention provides an anti-IL-1beta antibody for use in a method of inhibiting angiogenesis in an individual comprising administering to the individual an effective of the anti-IL-1beta antibody to inhibit angiogenesis. An "individual" according to any of the above embodiments is preferably a human.

In a further aspect, the invention provides for the use of an anti-IL-1beta antibody in the manufacture or preparation of a medicament. In one embodiment, the medicament is for treatment of an ocular vascular disease, preferably macular degeneration. In a further embodiment, the medicament is for use in a method of treating an ocular vascular disease, preferably macular degeneration, comprising administering to an individual having an ocular vascular disease, preferably macular degeneration, an effective amount of the medicament. In one such embodiment, the method further comprises administering to the individual an effective amount of at least one additional therapeutic agent, e.g., as described below. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating an ocular vascular disease, preferably macular degeneration. In one embodiment, the method comprises administering to an individual having such an ocular vascular disease, preferably macular degeneration, an effective amount of an anti-IL-1beta antibody. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in an individual. In one embodiment, the method comprises administering to the individual an effective amount of an anti-IL-1beta antibody to inhibit angiogenesis. In one embodiment, an "individual" is a human.

In a further aspect, the invention provides pharmaceutical formulations comprising any of the anti-IL-1beta antibodies provided herein, e.g., for use in any of the above therapeutic methods. In one embodiment, a pharmaceutical formulation comprises any of the anti-IL-1beta antibodies provided herein and a pharmaceutically acceptable carrier. In another embodiment, a pharmaceutical formulation comprises any of the anti-IL-1beta antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-VEGF antibody or an anti-ANG2 antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-IL-1beta antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-IL-1beta antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-IL-1beta antibody.

IV. Specific Embodiments

1. An antibody that specifically binds to human IL-1beta, wherein the antibody is a humanized variant of the murine antibody comprising the heavy chain variable domain of SEQ ID NO: 01 and the light chain variable domain of SEQ ID NO: 02.
2. A humanized antibody that specifically binds to human IL-1beta, wherein the humanized antibody comprises (a) a HVR-H1 comprising the amino acid sequence of SEQ ID NO: 18, (b) a HVR-H2 comprising the amino acid sequence of SEQ ID NO: 20, and (c) a HVR-H3 comprising the amino acid sequence of SEQ ID NO: 21.
3. A humanized antibody that specifically binds to human IL-1beta, wherein the humanized antibody comprises (a) a HVR-H1 comprising the amino acid sequence of SEQ ID NO: 25, (b) a HVR-H2 comprising the amino acid sequence of SEQ ID NO: 27, and (c) a HVR-H3 comprising the amino acid sequence of SEQ ID NO: 28.
4. A humanized antibody that specifically binds to human IL-1beta, wherein the humanized antibody comprises (a) a HVR-H1 comprising the amino acid sequence of SEQ ID NO: 32, (b) a HVR-H2 comprising the amino acid sequence of SEQ ID NO: 34, and (c) a HVR-H3 comprising the amino acid sequence of SEQ ID NO: 35.
5. The humanized antibody according to any one of embodiments 1 to 4, wherein the humanized antibody comprises (a) a HVR-L1 comprising the amino acid sequence of SEQ ID NO: 15; (b) a HVR-L2 comprising the amino acid sequence of SEQ ID NO: 16; and (c) HVR-L3 comprising the amino acid sequence of SEQ ID NO: 17.
6. The humanized antibody according to any one of embodiments 1 to 5, wherein the humanized antibody comprises in the heavy chain variable domain at position 48 an isoleucine amino acid residue, at position 67 an alanine amino acid residue, at position 69 a phenylalanine amino acid residue and at position 93 a valine amino acid residue and comprising in the light chain variable domain at position 36 the amino acid residue serine (numbering according to Kabat).
7. The humanized antibody according to any one of embodiments 1 to 6, wherein the humanized antibody comprises (a) a VH sequence having at least 95% sequence identity to the amino acid sequence of SEQ ID NO: 04, (b) a VL sequence having at least 95% sequence identity to the amino acid sequence of SEQ ID NO: 06, or (c) a VH sequence as in (a) and a VL sequence as in (b).
8. The humanized antibody according to any one of embodiments 1 to 7, wherein the humanized antibody comprises a VH sequence of SEQ ID NO: 04 and a VL sequence of SEQ ID NO: 06.
9. The antibody according to any one of embodiments 1 to 8, wherein the antibody is a humanized antibody.
10. An antibody that specifically binds to human IL-1beta comprising (a) a HVR-H1 comprising the amino acid sequence of SEQ ID NO: 39, (b) a HVR-H2 comprising the amino acid sequence of SEQ ID NO: 41, and (c) a HVR-H3 comprising the amino acid sequence of SEQ ID NO: 42.

11. The antibody according to embodiment 10, wherein the antibody further comprises (d) a HVR-L1 comprising the amino acid sequence of SEQ ID NO: 43, (e) a HVR-L2 comprising the amino acid sequence of SEQ ID NO: 44, and (f) a HVR-L3 comprising the amino acid sequence of SEQ ID NO: 45.

12. The antibody according to any one of embodiments 1 to 11, wherein the antibody is of the human subclass IgG1 or the human subclass IgG4.

13. The antibody according to any one of embodiments 1 to 12, wherein the antibody is of the human subclass IgG1 with a kappa light chain.

14. The antibody according to any one of embodiments 1 to 13, wherein the antibody is a monoclonal antibody.

15. An antibody comprising a VH sequence of SEQ ID NO: 04 and a VL sequence of SEQ ID NO: 06.

16. The antibody according to any one of embodiments 1 to 15, wherein the antibody is a bispecific antibody.

17. The antibody according to any one of embodiments 1 to 16, wherein the antibody specifically binds to human IL-1beta but does not bind to human IL-1alpha.

18. The antibody according to any one of embodiments 1 to 17, wherein the antibody blocks the biological activity of human IL-1beta by inhibiting the binding of human IL-1beta to human IL-1 receptors.

19. The antibody according to any one of embodiments 1 to 18, wherein the antibody specifically binds to two determinant sites on or close to the receptor binding site of IL-1beta.

20. The antibody according to any one of embodiments 1 to 19, wherein the antibody is a bivalent, bispecific antibody comprising
   a) a first light chain and a first heavy chain of an antibody specifically binding to a first antigen, and
   b) a second light chain and a second heavy chain of an antibody specifically binding to a second antigen, wherein the variable domains VL and VH of the second light chain and the second heavy chain are replaced by each other,
   wherein the first antigen or the second antigen is human IL-1beta.

21. The antibody according to embodiment 20, wherein the antibody comprises
   i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
   or
   ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

22. The antibody according to any one of embodiment 20 to 21, wherein the antibody comprises in the constant domain CL of the second heavy chain the amino acids at position 124 and 123 are substituted by K (numbering according to Kabat EU index).

23. The antibody according to any one of embodiment 20 to 22, wherein the antibody comprises in the constant domain CH1 of the second light chain the amino acids at position 147 and 213 are substituted by E (numbering according to EU index of Kabat).

24. The antibody according to any one of embodiment 20 to 23, wherein the antibody comprises in the constant domain CL of the first light chain the amino acids at position 124 and 123 are substituted by K, and in the constant domain CH1 of the first heavy chain the amino acids at position 147 and 213 are substituted by E (numbering according to Kabat EU index).

25. The antibody according to any one of embodiment 20 to 24, wherein the antibody comprises in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

26. The antibody according to any one of embodiments 1 to 19, wherein the antibody is a bivalent, bispecific antibody, comprising
   a) a first light chain and a first heavy chain of an antibody specifically binding to a first antigen, and
   b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other,
   wherein the first antigen or the second antigen is human IL-1beta.

27. The antibody according to any one of embodiments 1 to 19, wherein the antibody is a bivalent, bispecific antibody, comprising
   a) a first light chain and a first heavy chain of an antibody specifically binding to a first antigen, and
   b) a second light chain and a second heavy chain of an antibody specifically binding to a second antigen, wherein the constant domains CL and CH1 of the second light chain and the second heavy chain are replaced by each other,
   wherein the first antigen or the second antigen is human IL-1beta.

28. The antibody according to any one of embodiments 1 to 19, wherein the antibody is a multispecific antibody comprising
   a) a full length antibody specifically binding to a first antigen and consisting of two antibody heavy chains and two antibody light chains, and b) one, two, three or four single chain Fab fragments specifically binding to one to four further antigens (i.e. a second and/or third and/or fourth and/or fifth antigen, preferably specifically binding to one further antigen, i.e. a second antigen), wherein said single chain Fab fragments under b) are fused to said full length antibody under a) via a peptidic linker at the C- or N-terminus of the heavy or light chain of said full length antibody, wherein the first antigen or one of the further antigens is human IL-1beta.

29. The antibody according to any one of embodiments 1 to 19, wherein the antibody is a trivalent, bispecific antibody comprising a) a full length antibody specifically binding to a first antigen and consisting of two antibody heavy chains and two antibody light chains, b) a first polypeptide consisting of
ba) an antibody heavy chain variable domain (VH), or
bb) an antibody heavy chain variable domain (VH) and an antibody constant domain 1 (CH1),
wherein said first polypeptide is fused with the N-terminus of its VH domain via a peptidic linker to the C-terminus of one of the two heavy chains of said full length antibody, c) a second polypeptide consisting of
ca) an antibody light chain variable domain (VL), or
cb) an antibody light chain variable domain (VL) and an antibody light chain constant domain (CL),
wherein said second polypeptide is fused with the N-terminus of the VL domain via a peptidic linker to the C-terminus of the other of the two heavy chains of said full length antibody, and
wherein the antibody heavy chain variable domain (VH) of the first polypeptide and the antibody light chain variable domain (VL) of the second polypeptide together form an antigen-binding site specifically binding to a second antigen,
and
wherein the first antigen or the second antigen is human IL-1beta.

30. The antibody according to embodiment 29, wherein the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
i) heavy chain variable domain position 44 to light chain variable domain position 100, or
ii) heavy chain variable domain position 105 to light chain variable domain position 43, or
iii) heavy chain variable domain position 101 to light chain variable domain position 100 (numbering always according to Kabat EU index).

31. The antibody according to any one of embodiments 1 to 19, wherein the antibody is a trispecific or tetraspecific antibody, comprising
a) a first light chain and a first heavy chain of a full length antibody which specifically binds to a first antigen, and
b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
c) wherein one to four antigen binding peptides which specifically bind to one or two further antigens (i.e. to a third and/or fourth antigen) are fused via a peptidic linker to the C- or N-terminus of the light chains or heavy chains of a) and/or b), wherein the first antigen or the second antigen or one of the further antigens is human IL-1beta.

32. The antibody according to any one of embodiments 1 to 19, wherein the antibody is a bispecific, tetravalent antibody comprising
a) two light chains and two heavy chains of an antibody, which specifically bind to a first antigen (and comprise two Fab fragments),
b) two additional Fab fragments of an antibody, which specifically bind to a second antigen, wherein said additional Fab fragments are fused both via a peptidic linker either to the C- or N-termini of the heavy chains of a),
and
wherein in the Fab fragments the following modifications were performed
i) in both Fab fragments of a), or in both Fab fragments of b), the variable domains VL and VH are replaced by each other, and/or the constant domains CL and CH1 are replaced by each other,
or
ii) in both Fab fragments of a) the variable domains VL and VH are replaced by each other, and the constant domains CL and CH1 are replaced by each other, and
in both Fab fragments of b) the variable domains VL and VH are replaced by each other, or the constant domains CL and CH1 are replaced by each other,
or
iii) in both Fab fragments of a) the variable domains VL and VH are replaced by each other, or the constant domains CL and CH1 are replaced by each other, and
in both Fab fragments of b) the variable domains VL and VH are replaced by each other, and the constant domains CL and CH1 are replaced by each other,
or
iv) in both Fab fragments of a) the variable domains VL and VH are replaced by each other, and in both Fab fragments of b) the constant domains CL and CH1 are replaced by each other,
or
v) in both Fab fragments of a) the constant domains CL and CH1 are replaced by each other, and in both Fab fragments of b) the variable domains VL and VH are replaced by each other,
wherein the first antigen or the second antigen is human IL-1beta.

33. The antibody according to any one of embodiments 1 to 19, wherein the antibody is a bispecific, tetravalent antibody comprising:
a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
b) two light chains of said first antibody of a), c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and d) two (modified) light chains of said second antibody of c), each comprising a CL-CH1 domain pair, wherein the first antigen or the second antigen is human IL-1beta.

34. The antibody according to any one of embodiments 1 to 19, wherein the antibody is a bispecific antibody comprising a) the heavy chain and the light chain of a first full length antibody that specifically binds to a first antigen, and b) the heavy chain and the light chain of a second full length antibody that specifically binds to a second antigen, wherein the N-terminus of the heavy chain is connected to the C-terminus of the light chain via a peptidic linker, wherein the first antigen or the second antigen is human IL-1beta.

35. The antibody according to any one of embodiments 1 to 19, wherein the antibody is a bispecific antibody comprising a) a full length antibody specifically binding to a first antigen and consisting of two antibody heavy chains and two antibody light chains, and b) an Fv fragment specifically binding to a second antigen comprising a $VH^2$ domain and a $VL^2$ domain, wherein both domains are connected to each other via a disulfide bridge, wherein only either the $VH^2$ domain or the $VL^2$ domain is fused via a peptidic linker to the heavy or light chain of the full length antibody specifically binding to a first antigen, wherein the first antigen or the second antigen is human IL-1beta.

36. The antibody according to any one of embodiments 1 to 35, wherein the antibody comprises a first Fc-region polypeptide and a second Fc-region polypeptide, and wherein i) the first Fc-region polypeptide is selected from the group comprising
human IgG1 Fc-region polypeptide,
human IgG2 Fc-region polypeptide,
human IgG3 Fc-region polypeptide,
human IgG4 Fc-region polypeptide,
human IgG1 Fc-region polypeptide with the mutations L234A, L235A,
human IgG1 Fc-region polypeptide with the mutations Y349C, T366S, L368A, Y407V,
human IgG1 Fc-region polypeptide with the mutations S354C, T366S, L368A, Y407V,
human IgG1 Fc-region polypeptide with the mutations L234A, L235A, Y349C, T366S, L368A, Y407V,
human IgG1 Fc-region polypeptide with the mutations L234A, L235A, S354C, T366S, L368A, Y407V,
human IgG1 Fc-region polypeptide with the mutations P329G,
human IgG1 Fc-region polypeptide with the mutations L234A, L235A, P329G,
human IgG1 Fc-region polypeptide with the mutations P329G, Y349C, T366S, L368A, Y407V,
human IgG1 Fc-region polypeptide with the mutations P329G, S354C, T366S, L368A, Y407V,
human IgG1 Fc-region polypeptide with the mutations L234A, L235A, P329G, Y349C, T366S, L368A, Y407V,
human IgG1 Fc-region polypeptide with the mutations L234A, L235A, P329G, S354C, T366S, L368A, Y407V,
human IgG4 Fc-region polypeptide with the mutations S228P, L235E,
human IgG4 Fc-region polypeptide with the mutations S228P, L235E, P329G,
human IgG4 Fc-region polypeptide with the mutations Y349C, T366S, L368A, Y407V,
human IgG4 Fc-region polypeptide with the mutations S354C, T366S, L368A, Y407V,
human IgG4 Fc-region polypeptide with the mutations S228P, L235E, Y349C, T366S, L368A, Y407V,
human IgG4 Fc-region polypeptide with the mutations S228P, L235E, S354C, T366S, L368A, Y407V,
human IgG4 Fc-region polypeptide with the mutations P329G,
human IgG4 Fc-region polypeptide with the mutations P329G, Y349C, T366S, L368A, Y407V,
human IgG4 Fc-region polypeptide with the mutations P329G, S354C, T366S, L368A, Y407V,
human IgG4 Fc-region polypeptide with the mutations S228P, L235E, P329G, Y349C, T366S, L368A, Y407V,
human IgG4 Fc-region polypeptide with the mutations S228P, L235E, P329G, S354C, T366S, L368A, Y407V,
human IgG1, IgG2 or IgG4 with the mutations K392D, and
human IgG3 with the mutation N392D,
and ii) the second Fc-region polypeptide is selected from the group comprising
human IgG1 Fc-region polypeptide,
human IgG2 Fc-region polypeptide,
human IgG3 Fc-region polypeptide,
human IgG4 Fc-region polypeptide,
human IgG1 Fc-region polypeptide with the mutations L234A, L235A,
human IgG1 Fc-region polypeptide with the mutations S354C, T366W,
human IgG1 Fc-region polypeptide with the mutations Y349C, T366W,
human IgG1 Fc-region polypeptide with the mutations L234A, L235A, S354C, T366W,
human IgG1 Fc-region polypeptide with the mutations L234A, L235A, Y349C, T366W,
human IgG1 Fc-region polypeptide with the mutations P329G,
human IgG1 Fc-region polypeptide with the mutations L234A, L235A, P329G,
human IgG1 Fc-region polypeptide with the mutations P329G, S354C, T366W,
human IgG1 Fc-region polypeptide with the mutations P329G, Y349C, T366W,
human IgG1 Fc-region polypeptide with the mutations L234A, L235A, P329G, S354C, T366W,
human IgG1 Fc-region polypeptide with the mutations L234A, L235A, P329G, Y349C, T366W, human IgG4 Fc-region polypeptide with the mutations S228P, L235E,
human IgG4 Fc-region polypeptide with the mutations S228P, L235E, P329G,
human IgG4 Fc-region polypeptide with the mutations S354C, T366W,
human IgG4 Fc-region polypeptide with the mutations Y349C, T366W,
human IgG4 Fc-region polypeptide with the mutations S228P, L235E, S354C, T366W,
human IgG4 Fc-region polypeptide with the mutations S228P, L235E, Y349C, T366W,
human IgG4 Fc-region polypeptide with the mutations P329G,
human IgG4 Fc-region polypeptide with the mutations P329G, S354C, T366W,
human IgG4 Fc-region polypeptide with the mutations P329G, Y349C, T366W,
human IgG4 Fc-region polypeptide with the mutations S228P, L235E, P329G, S354C, T366W,
human IgG4 Fc-region polypeptide with the mutations S228P, L235E, P329G, Y349C, T366W,
human IgG1 with the mutations D399K, D356K, and/or E357K, and
human IgG2, IgG3 or IgG4 with the mutations D399K, E356K, and/or E357K.

37. The antibody according to any one of embodiments 1 to 35, wherein the antibody comprises a first Fc-region polypeptide and a second Fc-region polypeptide, and wherein
i) the first Fc-region polypeptide is a human IgG1 Fc-region polypeptide and the second Fc-region polypeptide is a human IgG1 Fc-region polypeptide, or
ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or
v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or
vi) the first Fc-region polypeptide is a human IgG4 Fc-region polypeptide and the second Fc-region polypeptide is a human IgG4 Fc-region polypeptide, or
vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or
viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or
ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or
x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

38. The antibody according to any one of embodiments 1 to 37, wherein the antibody comprises a first Fc-region polypeptide and a second Fc-region polypeptide, and wherein the antibody comprises the combination of mutations
i) I253A, H310A, and H435A, or
ii) H310A, H433A, and Y436A, or
iii) L251D, L314D, and L432D, or
iv) combinations of i) to iii)
in the first Fc-region polypeptide and in the second Fc-region polypeptide.

39. The antibody according to any one of embodiments 1 to 37, wherein the antibody comprises a first Fc-region polypeptide and a second Fc-region polypeptide, and wherein
a) the first and a second Fc-region polypeptide are both of human IgG1 or human IgG4 subclass (derived from human origin) and comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region, or
b) the first and a second Fc-region polypeptide both of human IgG1 or human IgG4 subclass (i.e. derived from human origin) and both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region, or
c) the first and a second Fc-region polypeptide both of human IgG1 or human IgG4 subclass (i.e. derived from human origin) and comprise the mutations I253 A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system).

40. The antibody according to any one of embodiments 1 to 37, wherein the antibody comprises a first Fc-region polypeptide and a second Fc-region polypeptide, and wherein
    a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
    b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
    c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a),
    wherein either the first Fc-region polypeptide or the second Fc-region polypeptide or both Fc-region polypeptides comprise independently of each other one of the following mutations or combination of mutations:
    T307H, or
    Q311H, or
    E430 H, or
    N434H, or
    T307H and Q311H, or
    T307H and E430H, or
    T307H and N434A, or
    T307H and N434H, or
    T307Q and Q311H, or
    T307Q and E430H, or
    T307Q and N434H, or
    T307H and Q311H and E430H and N434A, or
    T307H and Q311H and E430H and N434H, or
    T307H and Q311H and E430H and N434Y, or
    T307Q and Q311H and E430H and N434A, or
    T307Q and Q311H and E430H and N434H, or
    T307Q and Q311H and E430H and N434Y, or
    T307Q and V308P and N434Y and Y436H, or
    T307H and M252Y and S254T and T256E, or
    T307Q and M252Y and S254T and T256E, or
    Q311H and M252Y and S254T and T256E, or
    E430H and M252Y and S254T and T256E, or
    N434H and M252Y and S254T and T256E, or
    T307H and Q311H and M252Y and S254T and T256E, or
    T307H and E430H and M252Y and S254T and T256E, or
    T307H and N434A and M252Y and S254T and T256E, or
    T307H and N434H and M252Y and S254T and T256E, or
    T307Q and Q311H and M252Y and S254T and T256E, or
    T307Q and E430H and M252Y and S254T and T256E, or
    T307Q and N434H and M252Y and S254T and T256E, or
    T307H and Q311H and E430H and N434A and M252Y and S254T and T256E, or
    T307H and Q311H and E430H and N434H and M252Y and S254T and T256E, or
    T307H and Q311H and E430H and N434Y and M252Y and S254T and T256E, or
    T307Q and Q311H and E430H and N434A and M252Y and S254T and T256E, or
    T307Q and Q311H and E430H and N434H and M252Y and S254T and T256E, or
    T307Q and Q311H and E430H and N434Y and M252Y and S254T and T256E, or
    T307Q and V308P and N434Y and Y436H and M252Y and S254T and T256E.

41. The antibody according to any one of embodiments 1 to 37, wherein the antibody comprises a first Fc-region polypeptide and a second Fc-region polypeptide,
    and wherein the first Fc-region polypeptide comprises the mutations Y349C, T366S, L368A and Y407V (hole-chain) and the second Fc-region polypeptide comprises the mutations S354C and T366W (knob-chain),
    and wherein the first Fc-region polypeptide (hole-chain) comprises the mutations
    i) I253A or I253G, and
    ii) L314A or L314G or L314D,
    and wherein the first Fc-region polypeptide and the second Fc-region polypeptide are connected by one or more disulfide bridges,
    and wherein the CH3-domain of the first polypeptide and the CH3-domain of the second polypeptide both bind or both do not bind to protein A
    (numbering according to the Kabat EU index).

42. The antibody according to embodiment 41, wherein the antibody comprises the mutations
    i) I253A or I253G, and
    ii) L314A or L314G or L314D, and
    iii) T250Q, and/or
    iv) T256E or T256A.

43. The antibody according to any one of embodiments 41 to 42, wherein the antibody comprises the mutations
    i) I253A or I253G, and
    ii) L314A or L314G or L314D, and
    iii) optionally a) T250Q, and/or T256E or T256A, and.
    iv) a) L251A or L251G or L251D, and/or b) H310A or H310G.

44. The antibody according to any one of embodiments 41 to 43, wherein the antibody comprises the mutation
    i) I253A or I253G, and
    ii) L314A or L314G or L314D, and
    iii) a) T250Q, and/or T256E or T256A, and.
    iv) a) L251A or L251G or L251D, and/or b) H310A or H310G.
    v) optionally a) T307A or T307H or T307Q or T307P, and/or b) Q311H, and/or c) M252Y, and/or d) S254T.

45. The antibody according to any one of embodiments 41 to 44, wherein the antibody comprises the mutation
    i) T250Q, and/or
    ii) M252Y, and/or
    iii) S254T, and/or iv) T256E or T256A, and/or
v) T307A or T307H or T307Q or T307P, and/or
vi) Q311H.
46. An antibody according to any one of embodiments 1 to 45 for use as a medicament.
47. An antibody according to any one of embodiments 1 to 45 for use in the treatment of an ocular vascular disease.
48. Use of an antibody according to any one of embodiments 1 to 45 for the treatment of eye diseases, especially of ocular vascular diseases.
49. An antibody according to any one of embodiments 1 to 45 for use in treating an eye disease.
50. An antibody according to any one of embodiments 1 to 45 for use in treating eye diseases, especially ocular vascular diseases.
51. A method of treating an individual having an ocular vascular disease comprising administering to the individual an effective amount of an antibody according to any one of embodiments 1 to 45.
52. A pharmaceutical formulation comprising the antibody according to any one of embodiments 1 to 45.
53. A pharmaceutical formulation comprising the antibody according to any one of embodiments 1 to 45 for use in the treatment of ocular vascular diseases.
54. Use of the antibody according to any one of embodiments 1 to 45 for the manufacture of a medicament for the treatment of ocular vascular diseases.
55. A method of treatment of patient suffering from ocular vascular diseases by administering the antibody according to any one of embodiments 1 to 45 to a patient in the need of such treatment.
56. The pharmaceutical formulation according to any one of embodiments 52 to 53, wherein the antibody is administered via intravitreal application.
57. The administering according to any one of embodiments 55 to 56, wherein the administering is an intravitreal application.
58. A nucleic acid encoding the antibody according to any one of embodiments 1 to 45.
59. A cell comprising one or more nucleic acids encoding the antibody according to any one of embodiments 1 to 45.
60. A method for producing an antibody according to any one of embodiments 1 to 45, wherein the method comprises the following steps:
a) optionally transfecting a mammalian cell with one or more nucleic acids encoding the antibody according to any one of embodiments 1 to 45,
b) cultivating the cell to express the antibody, and
c) recovering the antibody from the cell or the cultivation medium and thereby producing the antibody.

V. Examples

The following are examples of methods and compositions of the invention. It is understood that various other embodiments may be practiced, given the general description provided above.

Example 1

Original Generation and Characterization of Murine Anti-IL1Beta Antibody H34

Materials—BALB/c female mice were obtained from Banting and Kingman (Freemont, Calif.). Complete and Incomplete Freud's Adjuvant (CFA and IFA) were from Difco (Detroit, Mich.). HB101 was from Hana Biologics, Inc. (Berkeley, Calif.). Dulbecco's Phosphate-Buffered Saline (PBS) without calcium and magnesium, and glutamine were from GIBCO Labs (Grand Island, N.Y.). Fetal bovine serum was from Hyclone Labs (Logan, Utah) and Hypoxanthine-Aminopterin-Thymidine (HAT) and Hypoxanthine-Thymidine (HT) supplements, and 50% polyethylene glycol (PEG) 1450 was from Bethesda Research Labs (Gaithersburg, Md.). Rabbit anti-mouse IgG+A+M peroxidase conjugate, streptavidin peroxidase, mouse Ig isotype identification kit and orthophenylene diamine (OPD) were from Zymed Labs (South San Francisco, Calif.). Sepharose protein-A and Sephadex G-25 were from Pharmacia (Piscataway, N.J.). Pristane (2,6,10,14-tetramethyl pentadecane) was from Aldrich Chem. Co. (Milwaukee, Wis.). $^{125}$I Bolton-Hunter reagent was from New England Nuclear (Boston, Mass.). All other chemicals were analytical grade from Sigma.

Hybridoma Production—Hybridomas to IL-1beta were produced using the method of Kohler and Milstein, supra as described by Lerner (1981) Yale J. Biol. Med., 54: 347. Twelve week old female BALB/c mice were injected intraperitoneally and in the hind footpads with 5 µg of purified MW 17,500 form of IL-1beta in CFA. Five booster injections in Incomplete Freund's Adjuvant (IFA) were given at 3-4 week intervals. Serum antibody titers were determined periodically by ELISA and after 5 injections a titer was detectable. The animal chosen for fusion received an intravenous (IV) boost of 10 µg of IL-1beta in sterile PBS. The spleen was removed 4 days later and the splenocytes fused with P3X63-Ag8.653 Myeloma cells using 50% PEG 1450. Cells were cultured in 96-well plates ($1*10^6$ cells/well) in HAT medium. Hybridoma supernatants were assayed for anti-IL-1beta activity by solid-phase antigen ELISA, solid-phase antibody RIA with $^{125}$IIL-1beta and inhibition of IL-1beta-induced thymocyte proliferation (see below). Hybridomas were cloned by limiting dilution in HAT medium with thymocytes ($5*10^5$/well) at least 3 times.

Antibody production and purification—Monoclonal antibody was produced in ascites by injecting $2*10^6$ hybridoma cells intraperitoneally into Pristane-treated mice (Kohler et al., supra). Ascites fluid was collected and antibody purified by sepharose-protein A chromatography (Goding, J. Immunol. Methods, 20 (1978) 241).

Monoclonal antibody ILB1-H34 was prepared from the corresponding cell lines as described above.

ELISA of IL-1beta antibody—Vinyl assay plates (Costar) were coated with 50 µL/well of a 5 µg/mL solution of antigen diluted in PBS and incubated overnight at 4 (degree) C. Wells were countercoated using 5% non-fat dry milk/0.05% Thimerosal/PBS one hour at room temperature. The wells were washed with 0.1% bovine serum albumin (BSA)/0.05% Thimerosal/PBS and 50 µL/well of anti-IL-1beta antibodies were incubated for 2 hours at room temperature. Antibody was detected by indirect ELISA using rabbit anti-mouse IgG+A+M peroxidase conjugate and OPD substrate solution. Alternatively, purified monoclonal antibody was biotinylated (Geusdon et al., J. Histochem. Cytochem. 27 (1979) 1131) and detected using streptavidin peroxidase and OPD substrate solution. Isotype of the monoclonal antibodies was identified by indirect ELISA using a mouse Ig isotype identification kit.

Thymocyte proliferation assay—IL-1beta and PHA (10 µg/ml) were added to cultures of C3H/HeJ mouse thymocytes ($1*10^6$/well) in MEM/5% fetal bovine serum (FBS)/100 µg/ml gentamicin, 2-mercaptoethanol ($2*10^{-5}$ M), 25 mM Hepes medium. After 48 hours at 37° C., 0.5 µCi/well of $^3$H thymidine was added and the cultures were incubated overnight. The cells were collected on glass fiber filters using a cell harvester and processed for scintillation counting.

Receptor binding assay—The 17,500 form of IL-1beta was labeled using diiodo $^{125}$I Bolton-Hunter reagent according to the manufacturer's instructions. One μg of IL-1beta in 10 μL of PBS was reacted with 1 mCi of reagent for 4 hours at 4° C.; 500 μL of PBS/0.2% gelatin was added and labeled IL-1beta was separated from free Bolton-Hunter reagent by chromatography on a 20*1 cm column of Sephadex G-25 with PBS/0.2% gelatin. $^{125}$IIL-1beta was added to confluent monolayers of BALB/c 3T3 fibroblasts in DMEM/1% BSA/0.1% sodium azide/0.01% Triton X-100 in 24-well culture plates. After 1 hour at 37° C. the monolayers were washed extensively in media without labelled IL-1beta. The monolayers were removed using 0.1 N NaOH for gamma counting. Non-specific binding of $^{125}$IIL-1beta was measured by incubating in the presence of 200-fold molar excess of unlabeled IL-1beta.

Determination of antibody affinity—Monoclonal antibody affinity was determined from data obtained using an immunoprecipitation radioimmunoassay. Briefly, 5000 cpm/tube of $^{125}$IIL-1beta was incubated with dilutions of purified monoclonal antibody in 0.3 ml of 1% non-fat dry milk/0.5% Thimerosal/PBS overnight at 4° C. Antigen-antibody complexes were precipitated by the addition of 100 μL/tube each of 10% normal mouse serum/PBS and 4 mg/ml goat anti mouse IgG sera in PBS. After 4 hours at 4° C., the 1/ml tube of ice-cold 2% polyethylene glycol-6000 was added and the tubes centrifuged at 3000*g for 20 min. at 4° C. The supernatants were aspirated and the pellets counted in a gamma counter. Affinity constants were calculated from bound/free ratios at different concentrations of antibody (Berson et al., Clin. Chim. Acta. 22 (1969) 51-69).

Affinity constants were calculated using data obtained from an immunoprecipitation radioimmunoassay (RIA) of $^{125}$IIL-1beta binding of different antibody concentrations as described above. The anti-IL-1beta antibody H34 has an affinity of $64*10^9$ L/mol for IL-1beta.

Example 2

Immunization of Mice

For immunization of NMRI mice, a RIMMS ("Rapid IMmunization, Multiple Sites") schedule was used.

Example 3

Determination of Anti-IL-1Beta Antibody Serum Titer

Human recombinant IL-1beta was immobilized on a 96-well NUNC Maxisorb plate at 2.5 μg/ml, 100 μl/well, in PBS, followed by: blocking of the plate with 2% CroteinC in PBS, 200 μl/well; application of serial dilutions of antisera, in duplicates, in 0.5% CroteinC in PBS, 100 μl/well; detection with HRP-conjugated goat anti-mouse IgG antibody (Jackson Immunoresearch) diluted 1:16,000 in 0.5% CroteinC in PBS, 100 μl/well. For all steps, plates were incubated for 1 hour at 37° C. Between all steps, plates were washed 3 times with 0.05 Tween 20 in PBS. Signal was developed by addition of BM Blue POD Substrate soluble (Roche Diagnostics GmbH, Mannheim, Germany), 100 μl/well; and stopped by addition of 1 M HCl, 100 μl/well.

Absorbance was read out at 450 nm, against 690 nm as reference. Titer was defined as dilution of antisera resulting in half-maximal signal.

Example 4

Human IL-1Beta Binding ELISA

Variant 1

The binding analysis was carried out using an enzyme-linked immunosorbent assay (ELISA)-based technology. The antigen human IL-1beta (Peprotech Cat. No 200-01B) was immobilized at a concentration of 500 ng/mL in 25 μL in PBS on a 384 well microtiter plate (Thermo Scientific, Cat. No. 464718). Every of the following steps was followed by a washing routine of 3 times 90 μL PBS with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The EC$_{50}$ was calculated with a four parameter logistic model using GraphPad Prism 6.0 software.

Variant 2

The binding analysis was carried out using an enzyme-linked immunosorbent assay (ELISA)-based technology. The antigen His-tagged human IL-1beta (Sino Biologics, Cat. No. 10139-H07E) was immobilized at a concentration of 0.25 μg/mL in 25 μL in PBS on a 384 well microtiter plate (Thermo Scientific, Cat. No. 464718). Every of the following steps was followed by a washing routine of 3 times 90 μL PBS, 0.5% BSA, 0.05 Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The EC$_{50}$ was calculated with a four parameter logistic model using GraphPad Prism 6.0 software.

Example 5

Cynomolgus IL-1Beta Binding ELISA

The binding analysis was carried out using an enzyme-linked immunosorbent assay (ELISA)-based technology. The antigen human IL-1beta (Sino Biologics, Cat. No. 90010CNAE) was immobilized at a concentration of 0.5 μg/mL in 25 μL in PBS on a 384 well microtiter plate (Thermo Scientific, Cat. No. 464718). Every of the following steps was followed by a washing routine of 3 times 90 μL PBS, 0.5% BSA, 0.05% Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Example 6

Murine IL-1Beta Binding ELISA

The binding analysis was carried out using an enzyme-linked immunosorbent assay (ELISA)-based technology. The antigen murine IL-1beta (Sino Biologics, Cat. No. 50101-MNAE) was immobilized at a concentration of 0.5 µg/mL in 25 µL in PBS on a 384 well microtiter plate (Thermo Scientific, Cat. No. 464718). Every of the following steps was followed by a washing routine of 3 times 90 µL PBS, 0.5% BSA, 0.05% Tween with dispense and aspiration: 1) blocking step: saturating unbound surface (1 hour, 2% BSA); 2) anti-IL-1beta antibody in increasing concentrations for 1 hour; 3) detection antibody, dilution=1:2000 (Donkey F(ab)$_2$ anti-rabbit IgG POD, Amersham, NA9340V or sheep IgG anti-mouse IgG POD, Amersham RPN4201). 20-30 min. after adding the substrate 3,3',5,5'-tetramethylbenzidine (TMB, Roche Diagnostics GmbH, Mannheim, Germany, Cat. No 11835033001) the optical density was determined at 370 nm. The $EC_{50}$ was calculated with a four parameter logistic model using GraphPad Prism 6.0 software.

Example 7

Protein-Protein Interaction Inhibition Assay: Human IL-1Beta:Human IL-1 Receptor Type 1

The protein-protein interaction inhibition analysis of human IL-1beta to the human IL-1 receptor type I was carried out using an enzyme-linked immunosorbent assay (ELISA)-based technology. The human His-tagged IL-1beta protein (Sino Biologics, Cat. No. 10139-H07E) was immobilized at a concentration of 1 µg/mL in 25 µL in PBS, 0.5% BSA and 0.05% Tween on a 384 well microtiter plate (Thermo Scientific Cat. No. 464718). Every of the following steps was followed by a washing routine of 3 times 90 µL PBS with dispense and aspiration: 1) blocking step saturating unbound surface (1 hour, 2% BSA); 2) 12.5 µL anti-IL-1beta antibody in increasing concentrations was incubated with 12.5 µL Fc-tagged human IL-1beta receptor (Sino Biologics, Ca. No 10126-H02H) at 300 ng/mL in a volume of 250 µL for 1 hour; 3) detection was achieved using peroxidase-labeled anti huFc antibody (Goat F(ab$_2$) anti-human FC POD, Jackson, Cat. No 109-036-098). 10-30 min. after adding the substrate 3,3',5,5'-tetramethylbenzidine (TMB, Roche Diagnostics GmbH, Cat. No. 11835033001) the optical density was determined at 370 nm. The $IC_{50}$ was calculated with a four parameter logistic model using GraphPad Prism 6.0 software.

Example 8

Protein-Protein Interaction Inhibition Assay: Human IL-1Beta:Human IL-1 Receptor Type 2

The protein-protein interaction inhibition analysis of human IL-1beta to the human IL-1 receptor type II was carried out using an enzyme-linked immunosorbent assay (ELISA)-based technology. The human His-tagged IL-1beta protein (Sino Biologics, Cat. No. 10139-H07E) was immobilized at a concentration of 1 µg/mL in 25 µL in PBS, 0.5% BSA and 0.05% Tween on a 384 well microtiter plate (Thermo Scientific, Cat. No. 464718). Every of the following steps was followed by a washing routine of 3 times 90 µL PBS with dispense and aspiration: 1) blocking step: saturating unbound surface (1 hour, 2% BSA); 2) 12.5 µL anti-IL-1beta antibody in increasing concentrations was incubated with 12.5 µL Fc-tagged human IL-1beta receptor (RnD, Ca. No. 663-2R-50) at 30 ng/mL in a volume of 250 µL for 1 hour; 3) detection was achieved using peroxidase-labeled anti-huFc antibody (Goat F(ab$_2$) anti-human FC POD, Jackson, Cat. No 109-036-098). 10-30 min. after adding the substrate 3,3',5,5'-tetramethylbenzidine (TMB, Roche Diagnostics GmbH, Mannheim, Germany, Cat. No. 11835033001) the optical density was determined at 370 nm. The $IC_{50}$ was calculated with a four parameter logistic model using GraphPad Prism 6.0 software.

Example 9

Expression of Mouse Hybridoma H34 Murine Anti-IL-1Beta Antibody Producing Hybridoma Medium contains following reagents: RPMI (PAN), 20% foetal calf serum, 2 mM Glutamine (PAN), 1x Sodium pyruvate (PAN), 1×NEAS (PAN)

Pre-thaw the frozen cell-containing-vial by placing the tube in a 37° C. water bath for 60 seconds. With 2 ml pre-warmed (37° C.) medium cells have been quickly resuspended and transferred from the vial into a 10 ml flask (CellStar); already containing 8 ml medium. Centrifuge flask for 5 minutes at 1000 rpm (25° C.). Then discard supernatant and resuspend gently cell-pellet by up-and-down-pipetting in 10 ml pre-warmed (37° C.) medium. Fill the whole solution in a T25-flask and place flask in an incubator (37° C., 7% $CO_2$, 85% humidity) for 2 days.

Split the cells the next 5 days each 2-3 days, by dilution in new medium, with a density of $1-2\times10^5$ cells/ml. Then start the following days to reduce part of foetal calf serum from 20% in a first step to 10%. After two splits in 10% foetal calf serum, mix medium (RPMI (PAN), 10% foetal calf serum, 2 mM Glutamine (PAN), 1× Sodium pyruvate (PAN), 1×NEAS (PAN)) 1:1 with Hyclone-ADCF-MAb-medium (Thermo-Scientific) and use this medium for another two splits. Then rise ratio of Hyclone: RPMI-with-10% foetal calf serum to 3:1 and seed cells with a higher density of $2-3\times10^5$ cells/ml. At least split cells in 100% Hyclone-medium added by Nutridoma CS (Roche Diagnostics GmbH, Mannheim, Germany).

Then expand volume of cells-solution to 20 ml (T75 flask) for 5 splits. For antibody-production fill 15 ml cells, with a density of $2.0\times10^6$ cells/ml in Celline CL1000 reactor and incubate for 8-9 days (37° C., 7% $CO_2$, 85% humidity). For harvesting, fill the supernatant in a 50 ml falcon and centrifuge with 4000 rpm 4 times (after each cycle the supernatant will be filled in a new 50 ml falcon). Finally freeze cell-free-supernatant at −20° C.

Example 10

Antibody Purification from Murine Hybridoma

Antibody-containing H34 hybridoma supernatant was filtered and purified by two chromatographic steps. The antibodies were captured by affinity chromatography using HiTrap Prot G (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.0, and immediately after elution neutralized to pH 6.0 with 1 M Tris-base, pH 9.0. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at −80° C.

Antibody-containing hybridoma supernatant was filtered and purified by two chromatographic steps. The supernatants were mixed with 50% v/v 2 M glycine, pH 8.6, 600 mM NaCl and were captured by affinity chromatography using HiTrap MabSelectSuRe (GE Healthcare) equilibrated with 1 M glycine, pH 8.6, 300 mM NaCl. Unbound proteins were removed by washing with equilibration buffer, and the antibody was recovered with 100 mM citrate buffer, pH 2.8 and immediately after elution neutralized to pH 6.0 with 1 M Tris-base, pH 8.5. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at −80° C.

Example 11

Transfection and Transient Expression of the Humanized Antibodies in HEK Cells

Transient expression of antibodies in suspension-adapted HEK293F (FreeStyle 293-F cells; Invitrogen) cells with Transfection Reagent 293-free (Novagen).

Cells have been passaged, by dilution, at least four times (volume 30 ml) after thawing in a 125 ml shake flask (Incubate/Shake at 37° C., 7% $CO_2$, 85% humidity, 135 rpm).

The cells were expanded to $3 \times 10^5$ cells/ml in 250 ml volume. Three days later, cells have been split and new seeded with a density of $7 \times 10^5$ cells/ml in a 250 ml volume in a 1 liter shake flask. Transfection will be 24 hours later at a cell density around $1.4$-$2.0 \times 10^6$ cells/ml.

Before transfection dilute 250 μg plasmid-DNA (122 μg light and 128 μg heavy chain) in a final volume of 10 ml with pre-heated (water bath; 37° C.) Opti-MEM (Gibco). Mix solution gentle and incubate at room temperature for not longer than 5 min. Then add 333.3 μl 293-free transfection reagent to DNA-OptiMEM-solution. Mix gently and incubate at room temperature for 15-20 minutes. Add whole volume of mixture to 1 L shake flask with 250 ml HEK-cell-culture-volume.

Incubate/Shake at 37° C., 7% $CO_2$, 85% humidity, 135 rpm for 6 or 7 days.

Harvest supernatant by a first centrifugation-step at 2,000 rpm, 4° C., for 10 minutes. Then transfer the supernatant in a new centrifugation-flask for a second centrifuge at 4,000 rpm, 4° C., for 20 minutes. Thereafter the cell-free-supernatant is filtered through a 0.22 μm bottle-top-filter and stored in a freezer (−20° C.).

Example 12

Antibody Purification from HEK Supernatant

The antibody-containing culture supernatants were filtered and purified by two chromatographic steps. The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 50 mM citrate buffer, pH 2.8, and immediately after elution neutralized to pH 6.0 with 1 M Tris-base, pH 9.0. Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at −80° C.

Example 13

Analytics of Antibody Preparations

The protein concentration of antibody preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit.

Aggregate content of antibody preparations was determined by high-performance SEC using a TSK-GEL QC-PAK GFC 300 using 2×PBS, pH 7.4 as running buffer or by high-performance SEC using a BioSuite High Resolution SEC, 250 Å, 5 μm analytical size-exclusion column (Waters GmbH) using 200 mM $K_2HPO_4$/$KH_2PO_4$, 250 mM KCl, pH 7.0 as running buffer.

Example 14

Preparation of Fab Fragment from an Antibody and Analytics 12 mg antibody (1 mg/ml in 20 mM Histidine, 140 mM NaCl, pH 6.0) were incubated with 240 μl L-cysteine solution (Merck Millipore; 250 mM in 20 mM Histidine, 140 mM NaCl, pH 6.0) and 327 μl Papain (Roche Life Science; 0.001 U/mg antibody) for 120 min at 37° C. After cleavage, affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4 was used for removal of intact IgG and Fc fragment. Subsequently, flow-through of MabSelectSuRe chromatography was further purified using size exclusion chromatography on Superdex 200™ (GE Healthcare) as second purification step. The size exclusion chromatography was performed in 20 mM histidine buffer, 0.14 M NaCl, pH 6.0. The Fab fragment containing solutions were concentrated with an Ultrafree-CL centrifugal filter unit equipped with a Biomax-SK membrane (Millipore, Billerica, Mass.) and stored at −80° C.

The protein concentrations of the Fab-fragments were determined by measuring the optical density (OD) at 280 nm, using the molar extinction coefficient calculated on the basis of the amino acid sequence.

Purity and integrity of the Fab-fragments were analyzed by SDS-PAGE (NuPAGE 4-12% Bis-Tris Gel, Invitrogen) in the presence and absence of a reducing agent (5 mM 1,4-dithiotreitol) and staining with Simply Blue Safe Stain (Invitrogen).

Aggregate content of Fab preparations was determined by high-performance SEC using a BioSuite High Resolution SEC, 250 A, 5 μm analytical size-exclusion column (Waters GmbH) using 200 mM $K_2HPO_4/KH_2PO_4$, 250 mM KCl, pH 7.0 as running buffer.

Example 15

ICAM-1 Expression after IL-1Beta Stimulation of A549 Cells

A549 cells (10,000/well) were gown overnight in RPMI 1640 supplemented with 10% FCS. Thereafter the medium was replaced by Hunger medium supplemented with 0.5% serum.

The anti-IL-1beta antibody was incubated for 2 hours with IL-1beta at 250 pg/ml and different concentrations of the antibody (1000, 100, 10, 1, 0.1, 0 ng/ml). Thereafter A549 cells were incubated overnight with the IL-1beta/antibody mixture in quadruplicates.

The cells were washed four times with ice cold PBS and thereafter fixed with PFA for 20 minutes. Thereafter the cells were blocked with GSDB, non-permeabilizing. After incubation for 2 hours with anti-ICAM-1 antibody (R&D Systems, 5 μg/ml) the sample was washed four times with PBS. For staining the sample was incubated for 1 hour with anti-mouse antibody-HRP conjugate (Amersham) diluted 1:1000. Afterwards the sample was washed four times with PBS and incubated for 2 hours with ABTS. Absorption was measured at 405 nm with a reference at 495 nm.

Example 16

IL-6 Determination after IL-1Beta Stimulation of A549 Cells (Quantikine ELISA, R&D Systems)

A549 cells (10,000/well) were gown overnight in RPMI 1640 supplemented with 10% FCS. Thereafter the medium was replaced by Hunger medium supplemented with 0.5% serum and the cultivation continued for 96 hours.

The anti-IL-1beta antibody (1 μg/ml) was incubated for 2 hours with IL-1beta at 250 pg/ml. Thereafter A549 cells were incubated overnight with the IL-1beta/antibody mixture in duplicates.

A sample of 100 μl of the cultivation supernatant was taken for further analysis.

A 96 well plate coated with a monoclonal anti-human IL-6 antibody was blocked for 15 min. with assay diluent RD1W. Thereafter the supernatant sample was added and incubated for 2 hours at RT. The wells were washed four times with 200 μl wash buffer each. Thereafter the wells were incubated with polyclonal anti-human IL-6 antibody conjugated to HRP at RT for two hours. The wells were washed four times with 200 μl wash buffer each. Afterwards the wells were incubated for 20 min. with tetramethyl benzidine and H202. The reaction was stopped by the addition of 2 N sulfuric acid after 20 min. Absorption was determined at 450 nm with a reference wavelength of 570 nm.

Example 17

Bioactivity Assay

Murine helper T lymphocyte (Th-2) D10.G4.1 line has been used extensively as a reliable and sensitive assay for IL-1 (interleukin-1) bioactivity, since D10 cells will proliferate only minimally to con A in the absence of IL-1 or feeder cells (see Symons, J. A., et al. in Lymphokines and Interferons, a Practical Approach. Clemens, M. J. et al. (Eds): IRL Press. 272 (1987)). The $ED_{50}$ for this effect is typically <12 pg/mL.

35,000 D10.G4.1 T-Cells/well (freshly thawed) are stimulated for 72 hours in IL-1beta (1 ng/ml) containing media (RPMI/2.5 μg/ml ConA/10% FCS).

Readout was determined by CellTiterGlo® Luminescent Cell Viability Assay according to the manufacturer's instructions.

Example 18

I-CAM1 Up-regulation on HUVEC Cells Induced by IL-1Beta

HUVEC cells (Lonza, Cat#00191027) in corresponding media EBM/EGM (Cat#CC-4176) were seeded out in a 96 well culture plate (Costar, Cat#3596) at 40,000 cells/well in EBM+2% BSA 200 μl/well. Cells were incubated to recover in a 5%-$CO_2$ incubator at 37° C. for 24 h. Two dilution series 40fold concentrated as finally requested were performed: one with the anti-IL-1b antibody huH34-2 and the other with recombinant human IL-1beta (R&D Systems, Cat#201-LB) in EBM+2% BSA. The two series were mixed against each other 1:1 and incubated for one hour at RT. 10 μl of this IL-1beta/anti-IL-1beta antibody mix was added to the cells and gently mixed. Incubation was performed in a 5%-$CO_2$ incubator at 37° C. for 20 hours. Thereafter all the media was removed from the cells and the cells were washed twice with PBS.

After one wash with Cell Dissociation Solution Non-enzymatic 1× (Sigma, Cat#C5914) an incubation with 100 μl of the Cell Dissociation Solution at 37° C. was done. Detachment was checked by observing by microscope every 5 minutes. When 80% of the cells became globate, cells were transferred into a FACS-Plate (96 well, 340 μl Storage, PP, V-bottom Plate (Falcon Cat#353263)). The remaining cells were detached from the culture plate with 100 μl PBS+1% BSA by aspirating 4 times and also added to the FACS-plate. After 5 min. centrifugation by 300×g the supernatant was discarded. Pellets were resuspended in 100 μl PBS+1% BSA+10 μg/ml human IgG (Sigma; Cat#I2511) AND Incubated for 15 min. at RT. 10 μl of anti-human ICAM-1 Fluorescein conjugate (CD54) (R&D Systems, Cat#BBA20) was added followed by an incubation at 4° C. for 30-45 min. After 5 min. centrifugation by 300×g the supernatant was discarded. The pellet was resuspended in 110 μl PBS+1% BSA and measured on LSRII.

Example 19

MSU Induced TNFalpha Production in THP1 Cells

THP1 cells (Invitrogen, Cat. No. thp-null) were grown until a density of 1×$10^6$ cells/ml in growth medium, RPMI 1640 (Gibco, Cat#A10491) supplemented with 10% FBS (heat inactivated) and transferred into a Falcon tube. PMA (phorbol myristate acetate, Invitrogen, Cat#tlrl-pma) was added with a final concentration of 300 ng/ml and incubated in the 5%-$CO_2$ incubator at 37° C. for 3 hours. Cells were washed once with PBS (5 min. centrifugation at 300×g, supernatant discarded) and resuspended with a density of 1.33×$10^6$ cells/ml in Hunger RPMI (Gibco, Cat#31870-025) supplemented with 2 mM L-Glutamine and 10% FBS (heat inactivated). 150 μl/well of the cell suspension was seeded out in a 96 well culture plate (Costar, Cat#3596) at 2×10$^5$ cells/well. Overnight incubation was performed in a 5%-$CO_2$ incubator at 37° C. 50 µl of a 4-fold concentrated MSU suspension, (monosodium urate crystals, Invitrogen, Cat#tlrl-msu) final concentration 250 µg/ml in Hunger medium, was added and incubated in the 5%-$CO_2$ incubator at 37° C. for 6 hours. Dilution series of the anti-IL-1beta antibodies were performed in growth medium. Supernatants from the THP1 cells were discarded and the wells were washed once with PBS. Then the prepared anti-IL-1b antibody dilution series were added to the wells. Overnight incubation was performed in a 5%-$CO_2$ incubator at 37° C. Supernatants were collected and analyzed by TNFalpha singleplex.

Example 20

Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore), aggregation (SEC) and fragmentation (capillary electrophoresis or SDS-PAGE) and compared with the untreated control.

Example 21

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering on a DynaPro Plate Reader (Wyatt) while the samples were heated with a rate of 0.05° C./min from 25° C. to 80° C.

Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase.

The melting temperature is defined as the inflection point in fluorescence intensity vs. wavelength graph.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 22

Binding Kinetics and Cross-reactivity of Anti-IL-1Beta Antibodies

Binding kinetics of anti-IL-1beta antibodies to human, cynomolgus, rat and murine IL-1beta as well as cross-reactivity to human IL-1beta and human IL-1alpha were investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human or anti-mouse Fc antibodies were immobilized on a Series S CM5 Sensor Chip (GE Healthcare) using standard amine coupling chemistry. Anti-IL-1beta antibodies were captured on the surface leading to a capturing response of 100-200 RU. IL-1beta molecules were injected for 90 s with concentrations from 0.74 up to 60 nM (1:3 dilution series) onto the surface (association phase). The dissociation phase was monitored for 600 sec by washing with running buffer. Cross-reactivity to human IL-1beta and human IL-1a was determined by a single injection of 100 nM antigen according to the conditions described above. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

Example 23

Binding Kinetics of Anti-IL-1Beta IgG Compared to Anti-IL-1Beta Fab

Binding of anti-IL-1beta IgG and Fab to human IL-1beta was investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human Fc or anti-human Fab antibodies were immobilized on a Series S CM5 Sensor Chip (GE Healthcare) using standard amine coupling chemistry. Anti-IL-1beta IgG and Fab was captured on the surface leading to a capturing response of approximately 100 and 50 RU, respectively. Human IL-1beta was injected for 90 s with concentrations from 0.74 up to 60 nM (1:3 dilution series) onto the surface (association phase) at a flow rate of 30 µl/min. The dissociation phase was monitored for 600 sec by washing with running buffer. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

Example 24

Mode of Action Analysis of Anti-IL-1Beta Antibodies

Binding inhibition of anti-IL-1beta to human IL-1RI was investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Human IL-1RI was immobilized on a Series S CM5 Sensor Chip (GE Healthcare) using standard amine coupling chemistry. 10 nM of human IL-1beta were pre-incubated with anti-IL-1beta antibodies concentrations from 100 nM down to 0.098 nM (1:2 dilution series). The IL-1beta/anti- IL-1beta antibody mixtures were injected onto the flow cell at 5 µl/min and the binding response (RU) after 60 s was used to monitor inhibition. The surface was regenerated by injecting 10 mM NaOH for 60 sec at a flow rate of 5 µl/min. Bulk refractive index differences were corrected by subtracting the response obtained from a mock surface.

Example 25

Production and Purification of Bispecific Antibodies

Transient expression of bispecific antibodies in suspension-adapted HEK293F (FreeStyle 293-F cells; Invitrogen) cells after transfection of DNA with Transfection Reagent 293-free (Novagen).

Cells have been passaged every third or fourth day, by dilution, at least four times (volume 30 ml) after thawing in a 125 ml shake flask (incubate/Shake at 37° C., 7% $CO_2$, 85% humidity, 135 rpm). The cells were expanded by seeding the cells with a cell density of $3\times10^5$ cells/ml in 250 ml medium. Three days later, cells have been split and newly seeded with a density of $2*10^5$ cells/ml in 500 ml medium. Four days later, cells have been split and newly seeded with a density of $7*10^5$ cells/ml in 1 liter medium (incubate/Shake at 37° C., 7% $CO_2$, 85% humidity, 110 rpm). Transfection was done 24 hours later at a cell density around $1.4-2.0\times10^6$ cells/ml.

Before transfection 1000 µg plasmid-DNA (2×250 µg light encoding plasmid DNA and 2×250 µg heavy chain encoding plasmid DNA) were diluted in a final volume of 40 ml with pre-heated (water bath; 37° C.) Opti-MEM (Gibco). The solutions were gently mixed and incubated at room temperature for not longer than 5 min. Then 1333 µl 293-free transfection reagent were added to the DNA-Opti-MEM-solution. The mixture was gently mixed and incubated at room temperature for 15-20 minutes. The whole volume of mixture was carefully added to the 1 liter HEK-cell-culture. The cells were further incubated with shaking at 110 rpm at 37° C., 7% $CO_2$, 85% humidity, for 7 days.

The supernatant was harvested after 7 days by a first centrifugation-step at 2000 rpm, 4° C., for 10 minutes. Then the supernatant was transferred into a new centrifugation-flask for a second centrifugation-step at 4000 rpm, 4° C., for 20 minutes. The cell-free-supernatant was filtered through a 0.22 µm filter (Millipore) and stored in a freezer (−20° C.) until purification-procedure was started.

The antibody-containing culture supernatants were filtered and purified by at least two chromatographic steps. The antibodies were captured by affinity chromatography using CaptureSelect Pre-packed Column IgG-CH1 (life technologies, #494320005) equilibrated with PBS (1 mM KH2PO4, 10 mM Na2HPO4, 137 mM NaCl, 2.7 mM KCl), pH 7.4. Unbound proteins were removed by washing with equilibration buffer, and antibodies were recovered with 25 mM citrate buffer, pH 3.0 and immediately after elution neutralized to pH 6.0 with 1 M Tris-base, pH 9.0.

Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass.) and stored at −80° C.

The protein concentration of antibody preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit.

Aggregate content of antibody preparations was determined by high-performance SEC using a BioSuite High Resolution SEC, 250 Å, 5 µm analytical size-exclusion column (Waters GmbH) using 200 mM K2HPO4/KH2PO4, 250 mM KCl, pH 7.0 as running buffer.

TABLE 35

| antibody | | scale [l] | yield [mg] | yield [mg/l supernatant] | Monomer (SE-HPLC) [%] | Monomer (CE-SDS) [%] | columns |
|---|---|---|---|---|---|---|---|
| anti-IL-1beta/ANG2 antibody | 0031 | 1 | 29.2 | 29.2 | >98 | >95 | CH1 select, SEC |
| anti-IL-1beta/VEGF antibody | 0032 | 1.5 | 23.6 | 15.7 | >98 | >95 | CH1 select, IEX, SEC |

Antibody 0031 is a CrossMab antibody comprising an IL-1beta binding site of SEQ ID NO: 04 (VH) and SEQ ID NO: 06 (VL) and an ANG2 binding site of SEQ ID NO: 53 (VH) and SEQ ID NO: 54 (VL).

Antibody 0032 is a CrossMab antibody comprising a VEGF binding site of SEQ ID NO: 55 (VH) and SEQ ID NO: 56 (VL) and an IL-1beta binding site of SEQ ID NO: 04 (VH) and SEQ ID NO: 06 (VL).

Example 26

Bispecific Antibody Kinetic Characterization

IL-1Beta:

Binding kinetics of anti-IL-1beta antibodies to human IL-1beta were investigated by surface plasmon resonance using a BIACORE T200 instrument (GE Healthcare). All experiments were performed at 25° C. using HBS-P (10 mM His, 140 mM NaCl, 0.05% Tween 20 pH 7.4) as running and dilution buffer. Anti-human Fc antibodies were immobilized on a Series S CM5 Sensor Chip (GE Healthcare) using standard amine coupling chemistry. Bispecific antibodies were captured on the surface leading to a capturing response of 100-200 RU. Human IL-1beta was injected for 90 s with concentrations from 0.74 up to 60 nM (1:3 dilution series) onto the surface (association phase). The dissociation phase was monitored for 600 sec by washing with running buffer. The surface was regenerated by injecting 3 M MgCl2 (for anti-human Fc antibody) or 10 mM Glycine pH 1.5 (for anti-mouse Fc antibody) for 60 sec at a flow rate of 5 µl/min. Bulk refractive index differences were corrected by subtracting the response obtained from a mock surface. Blank injections were subtracted (double referencing). The derived curves were fitted to a 1:1 Langmuir binding model using the BIAevaluation software.

ANG2:

Binding of the bispecific antibody to human ANG2-RBD-mouse Fc-region fusion was investigated by surface plasmon resonance using a BIACORE T200 instrument (GE Healthcare). Around 4000 RU of anti-mouse Fc-region antibody (10 µg/ml anti-mouse (Fc) antibody) were coupled on a Series S CM5 chip (GE Healthcare BR-1005-30) at pH 5.0 by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was HBS-P (10 mM HEPES, 150 mM NaCl pH 7.4, 0.05% Surfactant P20; GE Healthcare). The flow cell was set to 25° C.—and the sample block set to 12° C.—and primed with running buffer twice prior to kinetic characterization.

Human ANG2-RBD-murine Fc-region fusion was captured by injecting a 1 µg/ml solution for 30 sec. at a flow rate of 5 µl/min. Association was measured by injection of the bispecific antibody in various concentrations in solution for 90 sec. at a flow rate of 90 µl/min starting with 300 nM in serial 1:3 dilutions. The dissociation phase was monitored for up to 600 sec. and triggered by switching from the sample solution to running buffer. All surfaces were regenerated by 60 sec. washing with a 3 M MgCl2 solution at a flow rate of 5 µl/min. Bulk refractive index differences were corrected by subtracting the response obtained from an anti-mouse IgG antibody (Fc) surface. Blank injections were also subtracted (=double referencing). For calculation of KD and other kinetic parameters the Langmuir 1:1 model was used.

VEGF:

Binding of the bispecific antibody to human VEGF isoform 121 was investigated by surface plasmon resonance using a BIACORE T200 instrument (GE Healthcare). An anti-hexa-histidine antibody was coupled on a CM5 chip (GE Healthcare BR-1005-30) according to the manufacturer's instructions by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was HBS-P (10 mM HEPES, 150 mM NaCl pH 7.4, 0.05% Surfactant P20; GE Healthcare). The flow cell was set to 25° C.—and the sample block set to 12° C.—and primed with running buffer twice prior to kinetic characterization.

Histidine-tag comprising human VEGF isoform 121 was captured by injecting a solution for 30 sec. at a flow rate of 5 µl/min. Association was measured by injection of the bispecific antibody in various concentrations in solution for 90 sec. at a flow rate of 90 µl/min starting with 300 nM in serial 1:3 dilutions. The dissociation phase was monitored for up to 600 sec. and triggered by switching from the sample solution to running buffer. All surfaces were regenerated by 60 sec. washing with a 3 M MgCl2 solution at a flow rate of 5 µl/min. Bulk refractive index differences were corrected by subtracting the response obtained from an anti-hexa-histidine antibody surface. Blank injections were also subtracted (=double referencing). For calculation of KD and other kinetic parameters the Langmuir 1:1 model was used.

Example 27

X-ray Structure Determination

Apo Fab fragment H34

Crystallization screening for Fab fragment H34 was performed at a concentration of 32 mg/ml. Crystallization droplets were set up at 21° C. by mixing 0.1 µl of protein solution with 0.1 µl reservoir solution in vapor diffusion sitting drop experiments. Crystals appeared out of various conditions containing PEG as precipitating agent. Crystals used to determine the structure of H34 appeared within 2 days out of 0.1 M HEPES pH 7.0, 20% PEG 4000 and out of 0.1M sodium cacodylate, 15% PEG4000.

Crystals were harvested with dried Paraffin oil as cryo-protectant and then flash-cooled in liquid $N_2$. Diffraction images were collected with a Pilatus 6M detector at a temperature of 100K at the beam line X10SA of the Swiss Light Source and processed with the XDS package (Kabsch, W. Automatic processing of rotation diffraction data from crystals of initially unknown symmetry and cell constants. J. Appl. Cryst. 26 (1993) 795-800). Data from two crystals were merged to yield a 1.64 Å resolution data set in space group P1 and two Fab per crystallographic asymmetric unit (see Table below).

The structure was determined by molecular replacement using the Fab 577 from Roche-internal PDB-ID 1htfr as search model. The Fab was split into constant and variable domains and both used for separate searches in the CCP4 program PHASER CCP4 (CCP4 (Collaborative Computational Project, N. The CCP4 suite: programs for protein crystallography. Acta Crystallogr. D, (1994) 760-763) to account for possible changes in the elbow angle. The model was rebuilt in COOT (Emsley, P., Lohkamp, B., Scott, W G. & Cowtan, K. Features and development of COOT. Acta Crystallogr. D Biol. Crystallogr. 60 (2010) 486-501) and refined with CCP4 program.

TABLE 36

Data collection and structure refinement statistics for H34 Fab apo-crystal

| Data Collection | |
|---|---|
| Wavelength (Å) | 1.0 |
| Resolution[1] (Å) | 48.27-1.64 (1.699-1.64) |
| Space group | P1 |
| Unit cell (Å, °) | 50.03 69.72 80.58 93.389 95.059 110.195 |
| Total reflections | 424699 (40316) |
| Unique reflections | 123149 (12254) |
| Multiplicity | 3.4 (3.3) |
| Completeness (%) | 0.99 (0.99) |
| Mean I/σ(I) | 5.95 (0.59) |
| Wilson B-factor | 28.27 |
| R-merge [2] | 0.1151 (1.612) |
| R-meas | 0.1352 (1.908) |
| CC1/2 | 0.991 (0.332) |
| CC* | 0.998 (0.706) |
| Refinement | |
| Reflections used in refinement | 123149 (12068) |
| Reflections used for R-free | 6101 (592) |
| R-work [3] | 0.2005 (0.3964) |
| R-free [4] | 0.2350 (0.4117) |
| CC(work) | 0.959 (0.593) |
| CC(free) | 0.943 (0.586) |
| Number of non-hydrogen atoms | 7574 |
| macromolecules | 6622 |
| Protein residues | 859 |
| RMS bonds (Å) | 0.007 |

TABLE 36-continued

Data collection and structure refinement
statistics for H34 Fab apo-crystal

| | |
|---|---|
| RMS angles (°) | 1.09 |
| Ramachandran favored (%) | 97 |
| Ramachandran allowed (%) | 2.7 |
| Ramachandran outliers (%) | 0.23 |
| Rotamer outliers (%) | 1.1 |
| Clashscore | 1.30 |
| Average B-factor (Å²) | 32.58 |
| macromolecules | 31.78 |
| solvent | 38.12 |

All data computed with Phenix.
[1] Values in parentheses refer to the highest resolution bins.
[2] $R_{merge} = \Sigma |I - <I>|/\Sigma I$ where I is intensity.
[3] $R_{work} = \Sigma |F_o - <F_c>|/\Sigma F_o$ where $F_o$ is the observed and $F_c$ is the calculated structure factor amplitude.
[4] $R_{free}$ was calculated based on 5% of the total data omitted during refinement.

Complex Fab Fragment H34 with Human Il-1Beta

Prior to crystallization screening Fab fragment H34 was mixed with IL-1beta (Peprotech) in a molar ratio of 1.2:1. The protein mixture was incubated at 21° C. for 2 h. Protein concentration used in crystallization experiments was 32 mg/ml. Crystallization droplets were set up at 21° C. by mixing 0.1 μl of protein with 0.1 μl reservoir solutions in vapor diffusion sitting drop experiments. Crystals appeared out of 0.1 M Tris pH 8.0, 20% PEG 4000 within 2 days and grew to a final size of 0.15 mm×0.06 mm×0.01 mm within 4 days.

Crystals were harvested without addition of cryo-protectant and then flash frozen in liquid N2. Diffraction images were collected with a Pilatus 6M detector at a temperature of 100K at the beam line X10SA of the Swiss Light Source and processed with the XDS package (Kabsch, W. Automatic processing of rotation diffraction data from crystals of initially unknown symmetry and cell constants. J. Appl. Cryst. 26 (1993) 795-800 (1993)). Data collection and processing followed the same route as for the H34 apo crystal (see above). Statistics are collected in the Table above. Data from two crystals were merged to obtain a more complete dataset. Molecular replacement was successful using the H34 Fab structure and interleukin-1beta (PDB-ID 1I2h) as search models. Model building and refinement was performed as described above.

TABLE 37

Data collection and structure refinement statistics
for H34 Fab IL-1beta complex crystal

| Data Collection | |
|---|---|
| Wavelength | 1 |
| Resolution range [1] | 48.22-1.36 (1.409-1.36) |
| Space group | P 1 |
| Unit cell | 41.1 48.92 70.36 96.162 101.938 96.035 |
| Total reflections | 564817 (55575) |
| Unique reflections | 113220 (11310) |
| Multiplicity | 5.0 (4.9) |
| Completeness (%) | 0.99 (1.00) |
| Mean I/σ(I) | 9.82 (0.78) |
| Wilson B-factor | 17.64 |
| R-merge [2] | 0.09016 (2.448) |
| R-meas | 0.1007 (2.744) |
| CC1/2 | 0.999 (0.277) |
| CC* | 1 (0.659) |
| Refinement | |
| Reflections used in refinement | 113220 (10997) |
| Reflections used for R-free | 5663 (564) |
| R-work | 0.1559 (0.3786) |
| R-free | 0.2063 (0.4137) |
| CC(work) | 0.979 (0.659) |
| CC(free) | 0.971 (0.626) |
| Number of non-hydrogen atoms | 5318 |
| macromolecules | 4570 |
| Protein residues | 576 |
| RMS(bonds) | 0.005 |
| RMS(angles) | 1.09 |
| Ramachandran favoured (%) | 98 |
| Ramachandran allowed (%) | 1.9 |
| Ramachandran outliers (%) | 0 |
| Rotamer outliers (%) | 1.3 |
| Clashscore | 1.86 |
| Average B-factor | 28.68 |
| macromolecules | 26.52 |
| solvent | 41.85 |

All data computed with Phenix.
[1] Values in parentheses refer to the highest resolution bins.
[2] $R_{merge} = \Sigma |I - <I>|/\Sigma I$ where I is intensity.
[3] $R_{work} = \Sigma |F_o - <F_c>|/\Sigma F_o$ where $F_o$ is the observed and $F_c$ is the calculated structure factor amplitude.
[4] $R_{free}$ was calculated based on 5% of the total data omitted during refinement.

What is claimed is:

1. A humanized antibody that specifically binds to human and cynomolgus IL-1beta, wherein the humanized antibody comprises a heavy chain variable domain (VH) comprising (a) a HVR-H1 comprising the amino acid sequence of SEQ ID NO: 25, (b) a HVR-H2 comprising the amino acid sequence of SEQ ID NO: 26, (c) a HVR-H3 comprising the amino acid sequence of SEQ ID NO: 28, and a light chain variable domain (VL) comprising (d) a HVR-L1 comprising the amino acid sequence of SEQ ID NO: 15, (e) a HVR-L2 comprising the amino acid sequence of SEQ ID NO: 16, and (f) HVR-L3 comprising the amino acid sequence of SEQ ID NO: 17.

2. The humanized antibody of claim 1, wherein in the heavy chain variable domain at position 48 is an isoleucine amino acid residue, at position 67 is an alanine amino acid residue, at position 69 is a phenylalanine amino acid residue, and at position 93 is a valine amino acid residue; and wherein in the light chain variable domain at position 36 is a serine amino acid residue (numbering according to Kabat).

3. The humanized antibody of claim 1, wherein the antibody comprises (a) a VH amino acid sequence having at least 95% sequence identity to the amino acid sequence of SEQ ID NO: 04, (b) a VL amino acid sequence having at least 95% sequence identity to the amino acid sequence of SEQ ID NO: 06, or (c) a VH sequence as in (a) and a VL sequence as in (b).

4. The humanized antibody of claim 1, wherein the antibody comprises the VH amino acid sequence of SEQ ID NO:04 and VL amino acid sequence of SEQ ID NO: 06.

5. The humanized antibody of claim 1, wherein the humanized antibody is of the human subclass IgG1 or the human subclass IgG4.

6. The humanized antibody of claim 1 or claim 4, wherein the humanized antibody blocks the biological activity of human IL-1beta by inhibiting the binding of human IL-1beta to the human IL-1beta receptors.

7. A pharmaceutical composition comprising the antibody of claim 1 and a pharmaceutically acceptable carrier.

8. A pharmaceutical composition comprising the antibody of claim 4 and a pharmaceutically acceptable carrier.

9. The pharmaceutical composition of claim 7 or claim 8, further comprising an additional therapeutic agent selected from the group consisting of an anti-ANG2 antibody and an anti-VEGF antibody.

* * * * *

SEQUENCE LISTING

```
<160> NUMBER OF SEQ ID NOS: 60

<210> SEQ ID NO 1
<211> LENGTH: 118
<212> TYPE: PRT
<213> ORGANISM: Mus musculus

<400> SEQUENCE: 1

Glu Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Tyr Ile Ser Cys Tyr Asn Ala Phe Thr Thr Tyr Asn Gln Arg Phe
    50                  55                  60

Arg Gly Lys Ala Thr Phe Thr Val Asp Thr Ser Ser Ser Thr Ala Tyr
65                  70                  75                  80
```

```
Met Gln Phe Asn Ser Leu Thr Ser Glu Asp Ser Ala Val Tyr Tyr Cys
                85                  90                  95

Val Arg Ser Asp Tyr Tyr Gly Thr Ser Leu Tyr Trp Gly Gln Gly Thr
            100                 105                 110

Thr Leu Thr Val Ser Ser
        115

<210> SEQ ID NO 2
<211> LENGTH: 105
<212> TYPE: PRT
<213> ORGANISM: Mus musculus

<400> SEQUENCE: 2

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
                20                  25                  30

His Trp Ser Gln Gln Lys Ser Gly Ser Ser Pro Lys Leu Leu Ile Tyr
            35                  40                  45

Ser Thr Ser Asn Leu Ala Ser Gly Val Pro Ser Arg Phe Ser Gly Ser
50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Asn Tyr Tyr Thr Phe
                85                  90                  95

Gly Gly Gly Thr Lys Leu Glu Ile Lys
            100                 105

<210> SEQ ID NO 3
<211> LENGTH: 118
<212> TYPE: PRT
<213> ORGANISM: Artificial sequence
<220> FEATURE:
<223> OTHER INFORMATION: huH34-1 VH

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Tyr Ile Ser Ser Tyr Ser Gly Phe Thr Thr Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Tyr Tyr Gly Thr Ser Leu Tyr Trp Gly Gln Gly Thr
            100                 105                 110

Leu Val Thr Val Ser Ser
        115

<210> SEQ ID NO 4
<211> LENGTH: 118
<212> TYPE: PRT
<213> ORGANISM: Artificial sequence
<220> FEATURE:
```

<223> OTHER INFORMATION: huH34-2 VH

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser
        115

<210> SEQ ID NO 5
<211> LENGTH: 118
<212> TYPE: PRT
<213> ORGANISM: Artificial sequence
<220> FEATURE:
<223> OTHER INFORMATION: huH34-3 VH

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Ser Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser
        115

<210> SEQ ID NO 6
<211> LENGTH: 105
<212> TYPE: PRT
<213> ORGANISM: Artificial sequence
<220> FEATURE:
<223> OTHER INFORMATION: huH34 VK

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Ser Gln Gln Lys Pro Gly Gln Ala Pro Arg Leu Leu Ile Tyr

```
                35                  40                  45
Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys
            100                 105

<210> SEQ ID NO 7
<211> LENGTH: 118
<212> TYPE: PRT
<213> ORGANISM: Artificial sequence
<220> FEATURE:
<223> OTHER INFORMATION: huH34 test 1 VH

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Tyr Ile Ser Ser Tyr Asn Ala Phe Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Tyr Tyr Gly Thr Ser Leu Tyr Trp Gly Gln Gly Thr
            100                 105                 110

Leu Val Thr Val Ser Ser
        115

<210> SEQ ID NO 8
<211> LENGTH: 105
<212> TYPE: PRT
<213> ORGANISM: Artificial sequence
<220> FEATURE:
<223> OTHER INFORMATION: huH34 test 1 VK

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Tyr Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys
            100                 105
```

<210> SEQ ID NO 9
<211> LENGTH: 121
<212> TYPE: PRT
<213> ORGANISM: Mus musculus

<400> SEQUENCE: 9

Glu Val Gln Leu Gln Gln Ser Gly Pro Glu Leu Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Arg Gln Ser Asn Gly Lys Ser Leu Glu Trp Ile
        35                  40                  45

Gly Asn Ile Asp Pro Tyr Tyr Gly Gly Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Glu Gly Ser Pro Thr Arg Tyr Tyr Val Met Asp Tyr Trp Gly
            100                 105                 110

Gln Gly Thr Ser Val Thr Val Ser Ser
            115                 120

<210> SEQ ID NO 10
<211> LENGTH: 107
<212> TYPE: PRT
<213> ORGANISM: Mus musculus

<400> SEQUENCE: 10

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys His His Phe Tyr Asn Thr Pro Trp
                85                  90                  95

Thr Phe Gly Gly Gly Thr Lys Leu Glu Ile Lys
            100                 105

<210> SEQ ID NO 11
<211> LENGTH: 7
<212> TYPE: PRT
<213> ORGANISM: Mus musculus

<400> SEQUENCE: 11

Gly Tyr Ser Phe Thr Gly Tyr
1               5

<210> SEQ ID NO 12
<211> LENGTH: 3
<212> TYPE: PRT
<213> ORGANISM: Mus musculus

<400> SEQUENCE: 12

```
Tyr Asn Ala
1

<210> SEQ ID NO 13
<211> LENGTH: 17
<212> TYPE: PRT
<213> ORGANISM: Mus musculus

<400> SEQUENCE: 13

Tyr Ile Ser Cys Tyr Asn Ala Phe Thr Thr Tyr Asn Gln Arg Phe Arg
1               5                   10                  15

Gly

<210> SEQ ID NO 14
<211> LENGTH: 7
<212> TYPE: PRT
<213> ORGANISM: Mus musculus

<400> SEQUENCE: 14

Asp Tyr Tyr Gly Thr Ser Leu
1               5

<210> SEQ ID NO 15
<211> LENGTH: 6
<212> TYPE: PRT
<213> ORGANISM: Mus musculus

<400> SEQUENCE: 15

Ser Ser Ser Val Ser Tyr
1               5

<210> SEQ ID NO 16
<211> LENGTH: 3
<212> TYPE: PRT
<213> ORGANISM: Mus musculus

<400> SEQUENCE: 16

Ser Thr Ser
1

<210> SEQ ID NO 17
<211> LENGTH: 5
<212> TYPE: PRT
<213> ORGANISM: Mus musculus

<400> SEQUENCE: 17

Trp Ser Asn Tyr Tyr
1               5

<210> SEQ ID NO 18
<211> LENGTH: 7
<212> TYPE: PRT
<213> ORGANISM: Artificial sequence
<220> FEATURE:
<223> OTHER INFORMATION: huH34-1-HVR-H1

<400> SEQUENCE: 18

Gly Tyr Thr Phe Thr Gly Tyr
1               5

<210> SEQ ID NO 19
<211> LENGTH: 3
<212> TYPE: PRT
<213> ORGANISM: Artificial sequence
```

```
<220> FEATURE:
<223> OTHER INFORMATION: huH34-1-HVR-H2s

<400> SEQUENCE: 19

Tyr Ser Gly
1

<210> SEQ ID NO 20
<211> LENGTH: 17
<212> TYPE: PRT
<213> ORGANISM: Artificial sequence
<220> FEATURE:
<223> OTHER INFORMATION: huH34-1-HVR-H2

<400> SEQUENCE: 20

Tyr Ile Ser Ser Tyr Ser Gly Phe Thr Thr Tyr Ala Gln Lys Phe Gln
1               5                   10                  15

Gly

<210> SEQ ID NO 21
<211> LENGTH: 7
<212> TYPE: PRT
<213> ORGANISM: Mus musculus

<400> SEQUENCE: 21

Asp Tyr Tyr Gly Thr Ser Leu
1               5

<210> SEQ ID NO 22
<211> LENGTH: 6
<212> TYPE: PRT
<213> ORGANISM: Mus musculus

<400> SEQUENCE: 22

Ser Ser Ser Val Ser Tyr
1               5

<210> SEQ ID NO 23
<211> LENGTH: 3
<212> TYPE: PRT
<213> ORGANISM: Mus musculus

<400> SEQUENCE: 23

Ser Thr Ser
1

<210> SEQ ID NO 24
<211> LENGTH: 5
<212> TYPE: PRT
<213> ORGANISM: Mus musculus

<400> SEQUENCE: 24

Trp Ser Asn Tyr Tyr
1               5

<210> SEQ ID NO 25
<211> LENGTH: 7
<212> TYPE: PRT
<213> ORGANISM: Mus musculus

<400> SEQUENCE: 25

Gly Tyr Thr Phe Thr Gly Tyr
1               5
```

```
<210> SEQ ID NO 26
<211> LENGTH: 3
<212> TYPE: PRT
<213> ORGANISM: Mus musculus

<400> SEQUENCE: 26

Tyr Asn Ala
1

<210> SEQ ID NO 27
<211> LENGTH: 17
<212> TYPE: PRT
<213> ORGANISM: Artificial sequence
<220> FEATURE:
<223> OTHER INFORMATION: huH34-2-HVR-H2

<400> SEQUENCE: 27

Tyr Ile Ser Ser Tyr Asn Ala Phe Thr Thr Tyr Asn Gln Lys Phe Arg
1               5                   10                  15

Gly

<210> SEQ ID NO 28
<211> LENGTH: 7
<212> TYPE: PRT
<213> ORGANISM: Mus musculus

<400> SEQUENCE: 28

Asp Tyr Tyr Gly Thr Ser Leu
1               5

<210> SEQ ID NO 29
<211> LENGTH: 6
<212> TYPE: PRT
<213> ORGANISM: Mus musculus

<400> SEQUENCE: 29

Ser Ser Ser Val Ser Tyr
1               5

<210> SEQ ID NO 30
<211> LENGTH: 3
<212> TYPE: PRT
<213> ORGANISM: Mus musculus

<400> SEQUENCE: 30

Ser Thr Ser
1

<210> SEQ ID NO 31
<211> LENGTH: 5
<212> TYPE: PRT
<213> ORGANISM: Mus musculus

<400> SEQUENCE: 31

Trp Ser Asn Tyr Tyr
1               5

<210> SEQ ID NO 32
<211> LENGTH: 7
<212> TYPE: PRT
<213> ORGANISM: Mus musculus

<400> SEQUENCE: 32

Gly Tyr Thr Phe Thr Gly Tyr
1               5
```

<210> SEQ ID NO 33
<211> LENGTH: 3
<212> TYPE: PRT
<213> ORGANISM: Artificial sequence
<220> FEATURE:
<223> OTHER INFORMATION: huH34-3-HVR-H2s

<400> SEQUENCE: 33

Tyr Ser Ala
1

<210> SEQ ID NO 34
<211> LENGTH: 17
<212> TYPE: PRT
<213> ORGANISM: Artificial sequence
<220> FEATURE:
<223> OTHER INFORMATION: huH34-3-HVR-H2

<400> SEQUENCE: 34

Tyr Ile Ser Ser Tyr Ser Ala Phe Thr Thr Tyr Asn Gln Lys Phe Arg
1               5                   10                  15

Gly

<210> SEQ ID NO 35
<211> LENGTH: 7
<212> TYPE: PRT
<213> ORGANISM: Mus musculus

<400> SEQUENCE: 35

Asp Tyr Tyr Gly Thr Ser Leu
1               5

<210> SEQ ID NO 36
<211> LENGTH: 6
<212> TYPE: PRT
<213> ORGANISM: Mus musculus

<400> SEQUENCE: 36

Ser Ser Ser Val Ser Tyr
1               5

<210> SEQ ID NO 37
<211> LENGTH: 3
<212> TYPE: PRT
<213> ORGANISM: Mus musculus

<400> SEQUENCE: 37

Ser Thr Ser
1

<210> SEQ ID NO 38
<211> LENGTH: 5
<212> TYPE: PRT
<213> ORGANISM: Mus musculus

<400> SEQUENCE: 38

Trp Ser Asn Tyr Tyr
1               5

<210> SEQ ID NO 39
<211> LENGTH: 7
<212> TYPE: PRT
<213> ORGANISM: Mus musculus

```
<400> SEQUENCE: 39

Gly Tyr Ser Phe Thr Asp Tyr
1               5

<210> SEQ ID NO 40
<211> LENGTH: 3
<212> TYPE: PRT
<213> ORGANISM: Mus musculus

<400> SEQUENCE: 40

Tyr Tyr Gly
1

<210> SEQ ID NO 41
<211> LENGTH: 17
<212> TYPE: PRT
<213> ORGANISM: Mus musculus

<400> SEQUENCE: 41

Asn Ile Asp Pro Tyr Tyr Gly Gly Thr Thr Tyr Asn Gln Lys Phe Lys
1               5                   10                  15

Asp

<210> SEQ ID NO 42
<211> LENGTH: 10
<212> TYPE: PRT
<213> ORGANISM: Mus musculus

<400> SEQUENCE: 42

Gly Ser Pro Thr Arg Tyr Tyr Val Met Asp
1               5                   10

<210> SEQ ID NO 43
<211> LENGTH: 7
<212> TYPE: PRT
<213> ORGANISM: Mus musculus

<400> SEQUENCE: 43

Ser Glu Asn Ile Tyr Ser Asn
1               5

<210> SEQ ID NO 44
<211> LENGTH: 3
<212> TYPE: PRT
<213> ORGANISM: Mus musculus

<400> SEQUENCE: 44

Ala Ala Thr
1

<210> SEQ ID NO 45
<211> LENGTH: 6
<212> TYPE: PRT
<213> ORGANISM: Mus musculus

<400> SEQUENCE: 45

Phe Tyr Asn Thr Pro Trp
1               5

<210> SEQ ID NO 46
<211> LENGTH: 269
<212> TYPE: PRT
<213> ORGANISM: Homo sapiens
```

<400> SEQUENCE: 46

```
Met Ala Glu Val Pro Glu Leu Ala Ser Glu Met Met Ala Tyr Tyr Ser
1               5                   10                  15
Gly Asn Glu Asp Asp Leu Phe Phe Glu Ala Asp Gly Pro Lys Gln Met
            20                  25                  30
Lys Cys Ser Phe Gln Asp Leu Asp Leu Cys Pro Leu Asp Gly Gly Ile
        35                  40                  45
Gln Leu Arg Ile Ser Asp His His Tyr Ser Lys Gly Phe Arg Gln Ala
    50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                85                  90                  95
Ile Phe Glu Glu Glu Pro Ile Phe Phe Asp Thr Trp Asp Asn Glu Ala
            100                 105                 110
Tyr Val His Asp Ala Pro Val Arg Ser Leu Asn Cys Thr Leu Arg Asp
        115                 120                 125
Ser Gln Gln Lys Ser Leu Val Met Ser Gly Pro Tyr Glu Leu Lys Ala
    130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
            180                 185                 190
Lys Pro Thr Leu Gln Leu Glu Ser Val Asp Pro Lys Asn Tyr Pro Lys
        195                 200                 205
Lys Lys Met Glu Lys Arg Phe Val Phe Asn Lys Ile Glu Ile Asn Asn
    210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
Gln Asp Ile Thr Asp Phe Thr Met Gln Phe Val Ser Ser
            260                 265
```

<210> SEQ ID NO 47
<211> LENGTH: 107
<212> TYPE: PRT
<213> ORGANISM: Homo sapiens

<400> SEQUENCE: 47

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105

<210> SEQ ID NO 48
<211> LENGTH: 105
<212> TYPE: PRT
<213> ORGANISM: Homo sapiens

<400> SEQUENCE: 48

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 49
<211> LENGTH: 440
<212> TYPE: PRT
<213> ORGANISM: Artificial Sequence
<220> FEATURE:
<223> OTHER INFORMATION: CrossMab Ang2mut4 + huH34-2 HC1

<400> SEQUENCE: 49

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
```

```
                195                 200                 205
Glu Pro Lys Ser Cys Asp Lys Thr His Thr Cys Pro Pro Cys Pro Ala
210                 215                 220
Pro Glu Ala Ala Gly Gly Pro Ser Val Phe Leu Phe Pro Pro Lys Pro
225                 230                 235                 240
Lys Asp Thr Leu Met Ala Ser Arg Thr Pro Glu Val Thr Cys Val Val
                245                 250                 255
Val Asp Val Ser His Glu Asp Pro Glu Val Lys Phe Asn Trp Tyr Val
                260                 265                 270
Asp Gly Val Glu Val His Asn Ala Lys Thr Lys Pro Arg Glu Glu Gln
                275                 280                 285
Tyr Asn Ser Thr Tyr Arg Val Val Ser Val Leu Thr Val Leu Ala Gln
                290                 295                 300
Asp Trp Leu Asn Gly Lys Glu Tyr Lys Cys Lys Val Ser Asn Lys Ala
305                 310                 315                 320
Leu Gly Ala Pro Ile Glu Lys Thr Ile Ser Lys Ala Lys Gly Gln Pro
                325                 330                 335
Arg Glu Pro Gln Val Tyr Thr Leu Pro Pro Cys Arg Asp Glu Leu Thr
                340                 345                 350
Lys Asn Gln Val Ser Leu Trp Cys Leu Val Lys Gly Phe Tyr Pro Ser
                355                 360                 365
Asp Ile Ala Val Glu Trp Glu Ser Asn Gly Gln Pro Glu Asn Asn Tyr
370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn Ala Tyr Thr Gln Lys
                420                 425                 430
Ser Leu Ser Leu Ser Pro Gly Lys
                435                 440

<210> SEQ ID NO 50
<211> LENGTH: 448
<212> TYPE: PRT
<213> ORGANISM: Artificial Sequence
<220> FEATURE:
<223> OTHER INFORMATION: CrossMab Ang2mut4 + huH34-2 HC2

<400> SEQUENCE: 50

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Ile
            35                  40                  45
Gly Tyr Ile Ser Ser Tyr Asn Ala Phe Thr Thr Tyr Asn Gln Lys Phe
        50                  55                  60
Arg Gly Arg Ala Thr Phe Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Val Arg Ser Asp Tyr Tyr Gly Thr Ser Leu Tyr Trp Gly Gln Gly Thr
                100                 105                 110
Leu Val Thr Val Ser Ser Ala Ser Thr Lys Gly Pro Ser Val Phe Pro
```

```
            115                 120                 125
Leu Ala Pro Ser Ser Lys Ser Thr Ser Gly Gly Thr Ala Ala Leu Gly
        130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro Gly Lys
        435                 440                 445

<210> SEQ ID NO 51
<211> LENGTH: 236
<212> TYPE: PRT
<213> ORGANISM: Artificial Sequence
<220> FEATURE:
<223> OTHER INFORMATION: CrossMab Ang2mut4 + huH34-2 LC1

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
```

```
               35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Pro Gly Tyr Tyr Tyr
                100                 105                 110

Pro Ala Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 52
<211> LENGTH: 212
<212> TYPE: PRT
<213> ORGANISM: Artificial Sequence
<220> FEATURE:
<223> OTHER INFORMATION: CrossMab Ang2mut4 + huH34-2 LC2

<400> SEQUENCE: 52

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
                 20                  25                  30

His Trp Ser Gln Gln Lys Pro Gly Gln Ala Pro Arg Leu Leu Ile Tyr
                 35                  40                  45

Ser Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys His Gln Trp Ser Asn Tyr Tyr Thr Phe
                 85                  90                  95

Gly Gln Gly Thr Lys Leu Glu Ile Lys Arg Thr Val Ala Ala Pro Ser
                100                 105                 110

Val Phe Ile Phe Pro Pro Ser Asp Arg Lys Leu Lys Ser Gly Thr Ala
                115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
```

165                 170                 175
Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 53
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VH

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser

<210> SEQ ID NO 54
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VL

<400> SEQUENCE: 54

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser
            100                 105                 110

<210> SEQ ID NO 55
<211> LENGTH: 123
<212> TYPE: PRT
<213> ORGANISM: Artificial sequence
<220> FEATURE:
<223> OTHER INFORMATION: VEGF_LC VHVL cross LC kappa

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120
```

<210> SEQ ID NO 56
<211> LENGTH: 107
<212> TYPE: PRT
<213> ORGANISM: Artificial sequence
<220> FEATURE:
<223> OTHER INFORMATION: VEGF_LC10 VHVL cross IgG HC LALAPGAAA knob

<400> SEQUENCE: 56

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 57
<211> LENGTH: 440
<212> TYPE: PRT
<213> ORGANISM: Artificial Sequence
<220> FEATURE:
<223> OTHER INFORMATION: CrossMab Ang2mut5 + huH34-2 HC1

<400> SEQUENCE: 57

```
Ser Tyr Val Leu Thr Gln Pro Pro Ser Val Ser Val Ala Pro Gly Gln
1               5                   10                  15
```

```
Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Thr Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp Lys Thr His Thr Cys Pro Pro Cys Pro Ala
210                 215                 220

Pro Glu Ala Ala Gly Gly Pro Ser Val Phe Leu Phe Pro Pro Lys Pro
225                 230                 235                 240

Lys Asp Thr Leu Met Ala Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu Ala Gln
    290                 295                 300

Asp Trp Leu Asn Gly Lys Glu Tyr Lys Cys Lys Val Ser Asn Lys Ala
305                 310                 315                 320

Leu Gly Ala Pro Ile Glu Lys Thr Ile Ser Lys Ala Lys Gly Gln Pro
                325                 330                 335

Arg Glu Pro Gln Val Tyr Thr Leu Pro Pro Cys Arg Asp Glu Leu Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn Ala Tyr Thr Gln Lys
            420                 425                 430

Ser Leu Ser Leu Ser Pro Gly Lys
```

<210> SEQ ID NO 58
<211> LENGTH: 448
<212> TYPE: PRT
<213> ORGANISM: Artificial Sequence
<220> FEATURE:
<223> OTHER INFORMATION: CrossMab Ang2mut5 + huH34-2 HC2

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Tyr Ile Ser Ser Tyr Asn Ala Phe Thr Thr Tyr Asn Gln Lys Phe
    50                  55                  60

Arg Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Asp Tyr Tyr Gly Thr Ser Leu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
```

```
              355                 360                 365
Ala Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn Ala Tyr Thr Gln Lys Ser Leu Ser Leu Ser Pro Gly Lys
        435                 440                 445

<210> SEQ ID NO 59
<211> LENGTH: 236
<212> TYPE: PRT
<213> ORGANISM: Artificial Sequence
<220> FEATURE:
<223> OTHER INFORMATION: CrossMab Ang2mut5 + huH34-2 LC1

<400> SEQUENCE: 59

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Asn Phe Ala Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Ser Ser Pro Gly Tyr Tyr Tyr
            100                 105                 110
Pro Ala Ala Phe Asp Ile Trp Gly Gln Gly Thr Met Val Thr Val Ser
        115                 120                 125
Ser Ala Ser Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 60
<211> LENGTH: 212
<212> TYPE: PRT
<213> ORGANISM: Artificial Sequence
<220> FEATURE:
<223> OTHER INFORMATION: CrossMab Ang2mut5 + huH34-2 LC2
```

```
<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
                20                  25                  30

His Trp Ser Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Asn Tyr Tyr Thr Phe
                85                  90                  95

Gly Gln Gly Thr Lys Leu Glu Ile Lys Arg Thr Val Ala Ala Pro Ser
                100                 105                 110

Val Phe Ile Phe Pro Pro Ser Asp Arg Lys Leu Lys Ser Gly Thr Ala
            115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
            195                 200                 205

Arg Gly Glu Cys
        210
```